US006831208B1

(12) United States Patent
Chiang et al.

(10) Patent No.: US 6,831,208 B1
(45) Date of Patent: Dec. 14, 2004

(54) 4-COUMARATE CO-ENZYME A LIGASE PROMOTER

(75) Inventors: Vincent Lee C. Chiang, Hancock, MI (US); Chung-Jui Tsai, Hancock, MI (US); Wen-Jing Hu, Houston, TX (US)

(73) Assignee: Board of Control of Michigan Technological University, Houghton, MI (US)

( * ) Notice: Subject to any disclaimer, the term of this patent is extended or adjusted under 35 U.S.C. 154(b) by 0 days.

(21) Appl. No.: 09/530,663

(22) PCT Filed: Nov. 12, 1998

(86) PCT No.: PCT/US98/24138

§ 371 (c)(1),
(2), (4) Date: Jul. 11, 2000

(87) PCT Pub. No.: WO99/24561

PCT Pub. Date: May 20, 1999

Related U.S. Application Data

(63) Continuation-in-part of application No. 08/969,046, filed on Nov. 12, 1997, now Pat. No. 6,455,762.

(51) Int. Cl.$^7$ .......................... A01H 1/00; A01H 5/00; C12N 15/82; C12N 5/10; C12N 15/10

(52) U.S. Cl. ...................... 800/298; 800/278; 800/287; 536/24.1; 435/468; 435/320.1

(58) Field of Search ................................ 800/287, 290, 800/298, 278; 435/419, 468, 320.1; 536/24.1

(56) References Cited

U.S. PATENT DOCUMENTS

| | | | |
|---|---|---|---|
| 4,940,838 A | | 7/1990 | Schilperoort et al. |
| 5,107,065 A | | 4/1992 | Shewmaker et al. |
| 5,190,931 A | | 3/1993 | Inouye |
| 5,451,514 A | | 9/1995 | Boudet et al. |
| 5,489,520 A | | 2/1996 | Adams et al. |
| 5,545,526 A | * | 8/1996 | Baxter-Lowe .................. 435/6 |
| 5,554,798 A | | 9/1996 | Lundquist et al. |
| 5,850,020 A | | 12/1998 | Bloksberg et al. |
| 5,952,486 A | | 9/1999 | Bloksberg et al. |
| 6,204,434 B1 | | 3/2001 | Bloksberg et al. |
| 6,268,549 B1 | | 7/2001 | Sailland et al. |
| 6,303,847 B1 | | 10/2001 | Kawaoka et al. |
| 6,420,629 B1 | * | 7/2002 | Xue et al. .................... 800/284 |
| 6,455,762 B1 | | 9/2002 | Chiang et al. |

FOREIGN PATENT DOCUMENTS

| | | |
|---|---|---|
| WO | WO 93/05160 | 3/1993 |
| WO | WO 95/06128 | 8/1994 |
| WO | WO 96/38567 | 12/1996 |
| WO | WO 98/11205 | 3/1998 |

OTHER PUBLICATIONS

Hao et al. Unique Mode of GCC Box Recognition by the DNA–binding Domain of Ethylene–responsive Element–binding Factor (ERF Domain) in Plant, 1998. The Journal of Biological Chemistry vol. 273, No. 41, pp. 26857–26861.*
Bush et al. Activation of a Floral Homeotic Gene in Arabidopsis, 1999. Science vol. 285 pp. 585–587.*
Lohmann et al. A Molecular Link between Stem Cell Regulatio and Floral Patterning in Arabidopsis, 2001. Cell, vol. 105, 793–803.*
Lzawa et al. Plant bZIP Protein DNA Binding Specificity, 1993. J. Mol. Biol. 230, 1131–1144.*
Commen et al. The Elicitor–Inducible Alfalfa Isoflavone Reductase Promoter Confers Different Patterns Of Developmental Expression in Homologous and Heterologous Transgenic Plants, 1994. The Plant Cell, vol. 6, 1789–1803.*
Grattapaglia et al. Lobiolly pine fusiform rust deaease resistance marker OPC6 primer, 1996.*
Baxter–Lowe et al. Method for HLA Typing, 1996. Patent : US 5545526–A 16.*
Adler et al., *Wood Sci. Technol.*, 11, 169–218 (1977).
Allina et al., Isolation and characterization of the 4–coumarate: CoA ligase gene family in a popular hybrid (abstract No. 852) *Plant Physiol.* 105 (supplement) 154 (1994).
Arioli et al., *Science*, 279, 717–720 (1997).
Atalla et al., *Science*, 277, 636–638 (1985).
Baucher et al., *Plant Physiol.*, 112, 1479–1490 (1996).
Becker–Andre et al.,*J. Biol. Chem.*, 266, 8551–8559 (1991).
Bjorkman, *Nature*, 174, 1057 (1954).
Brasileiro et al., *Plant Mol. Bio* 17:441–452 (1991).
Braunschweiler et al.,*J. Magn. Reson.*, 53, 521–528 (1983).
Buchanan–Wollaster et al., *J. Cell Biochem.*, 130, 330 Abstract No. M503 (1989).
Bugos RC et al., *Biotechniques* 19(5):734–737 (1995).
Caldwell et al., *Physiol. Plant*, 58, 445–450 (1983).
Chen, Ph.D. Thesis, North Carolina State University, Raleigh, North Carolina (1991).
Chiang et al., *Holzforshung*, 44:147–155 (1990).
Chiang, et al., *Wood Sci. Technol.*, 17, 217–226 (1983).
Ciucanu et al., *Carbohydr. Res.*, 131, 209–217 (1984).
Datla et al., *Plant Sci.*, 94, 139–149 (1993).
Davis, J., *Wood Chem. Technol.*, 18, 235–252 (1998).
DeBlock, *Plant Physiol.* 93:1110–1116 (1990).
Doerner, et al., *Nature*, vol. 380, 520–523 (Apr. 11, 1996).
Douglas et al., *EMBO Journal* 10(7): 1767–1775 (1991).
Ehlting, et al. *The Plant Journal*, 19(1):9–20 (1991).
Elkind et al., *Proc. Natl. Acad. Sci. USA*, 87, 9057–9061 (1990).
GenBank Accession No. M62755, 1993.
GenBank Accession No. U12012, 1996.
GenBank Accession No. U12013, 1996.

(List continued on next page.)

*Primary Examiner*—Amy J. Nelson
*Assistant Examiner*—Stuart F. Baum
(74) *Attorney, Agent, or Firm*—Michael Best & Friedrich LLP

(57) ABSTRACT

The present invention provides a Populus 4-coumarate Co-enzyme A ligase gene promoter that directs expression in the xylem of plants. The promoter is used in methods designed to alter lignin content, lignin structure, cellulose content and combinations thereof. The methods comprise operably linking said promoter to heterologous nucleic acid molecules.

7 Claims, 16 Drawing Sheets

OTHER PUBLICATIONS

GenBank Accession No. X13324, 1993.
GenBank Accession No. X52623, 1993.
Hahlbrook et al., *Proc. Natl. Acad. Sci. USA,* 92, 4150–4157 (1995).
Hakomori, *J. Biochem.* Tokyo, 55, 205–208 (1964).
Halpin et al., *Plant J.,* 6(3) 339–350 (1994).
Hartley, *J. Chromatogr.,* 54, 335–344 (1971).
Hibino et al., *Biosci. Biotech. Biochem.,* 59(5) 929–931 (1995).
Higuchi, *Biochemistry and Molecular Biology of Wood,* Springer Series in Wood Science. T.E. Timell ed. (1997).
Holmberg, et al., *Nature Biotechnology* vol. 15, 244–247 (Mar. 1996).
Holsters et al., *Mol. Gen. Genet.* 163:181–187 (1978).
Horsch R.B., *Plant Molecular Biology Manual,* A5:1–9 (1988).
Houtman et al., *Plant Physiol.,* 107, 977–984 (1995).
Howe et al., *Woody Plant Biotech,* Plenum Press, New York, pp. 283–294 (1991).
Hu, Wen–Jing, Isolation and Characterization of p–coumarate Co–enzyme A Ligase cDNAs and Genes from Quaking Aspen (*Populus tremuloides* Michx), Ph.D Dissertation, Michigan Technological University, Houghton, Michigan (1997).
Jorgensen, et al., *Plant Mol Biol* Aug. 1996;31(5):957–73.
Kajita et al., *Plant Physiol.,* 114, 871–879 (1997).
Kawaoka A., Chiang VL, *Proceedings of the 6th International Conference on Biotechnology in the Pulp Paper Industry,* Vienna, Austria (1995).
Klopfenstein et al., *Can. J. For. Res.* 21:1321–1328 (1991).
Lee et al., *Plant Cell,* 9, 1985–1998 (1997).
Leple et al., *Plant Cell Reports* 11:137–141 (1992).
Li et al., *Plant Cell,* 13(7): 1567–1585 (2001).
Lloyd et al., *Proc. Int. Plant Prop. Soc.,* 30:421–437 (1980).
Logemann et al., *Plant J.,* 8, 865–876 (1995).
Logemann et al., *Proc. Natl. Acad. Sci. USA,* 92, 5905–5909 (1995).
McGranahan et al., *Plant Cell Reports,* 8:512–616 (1990).
Nilsson et al., *Transgenic Res.* 1:209–220 (1992).
Osakabe et al., *Proc. Natl. Acad. Sci. USA,* 96:8955–8960 (1999).
Palmer et al., *J. Magn. Reson. Ser. A.,* 111, 70 (1991).
Parsons et al. *Bio/Technology* 4:533–536 (1986).
Pettersen, R.C. and Schwandt, J., et al., *J. Wood Chem & Technol.,* 11:495–501 (1991).
Piquemal et al., *Plant J.,* 13(1) 71–83 (1998).
Pythoud et al., *Bio/Technology* 5:1323–1327 (1987).
Que, et al., *Plant Journal* 13 (3): 401–409 Feb. 1998.
Ralph et al., *JACS,* 116, 9448–9456 (1994).
Ruiz–Cabello et al., *J. Magn. Reson.,* 100, 282–302 (1992).
Sambrook et al., *Molecular Cloning: A Laboratory Manual,* Cold Spring Harbor Laboratory Press, NY (1989). Just table of contents.
Schmelzer et al., *Plant Cell,* 1, 993–1001 (1989).
Sewalt et al., *Plant Phyiol.,* 115, 41–50 (1997).
Shin et al., *Biotech. Ag. & Forestry,* 29 321 (1994).
Shirley, *Trends in Plant Sci.,* 1(11) 377–382 (1996).
Szerszen, et al., *Science* vol. 265, 1699–1701 (Sep. 16, 1994).
Taylor et al., *Plant J.,* 2, 959–970 (1992).
Tsai et al., *Plant Physiol.,* 117, 101–102 (1998).
Turner et al., *Plant Cell,* 9, 689–701 (1997).
Uhlmann et al., *Plant Phsiol.,* 102:1147–1156. (1993).
Watson et al., Recombinant DNA 1992, W.H. Freeman and Company, N.Y., Just table of contents.
White et al., *Nature,* 205, 818 (1965).
Zhang, X–H et al., *Plant Physiol,* 113:65–74 (1997).
Ronaldo et al, Thioacidolysis, Methods in Lignin Chemistry, Springer–Verlag, Berlin, pp 334–349 (1992).
Altenbach, et al, Plant Molecular Biology, 13: 513–522 (1989).
Atanassova et al, The Plant Journal, 8(4), 465–477 (1995).
Brasileiro et al, Transgenic Research, 1: 133–141 (1992).
Brunke et al, Trends in Biotech, 9: 197–200 (1991).
Dandekar et al, Bio/Technology, 5: 587–590 (1987).
Dwivedi et al, Plant Molecular Biology 26: 61–71 (1994).
Filho et al, Plant Cell Reports, 13: 666–670 (1994).
Fillatti et al, Mol. Gen. Genet., 206: 192–199 (1987).
Hu et al, Proc. Natl. Acad. Sci., 95: 5407–5412 (1998).
Huang et al, In Vitro Cell Dev. Biol., 27P: 201–207 (1991).
Kajita et al, Plant Cell Physiol., 37(7): 957–965 (1996).
Keller et al, Transgenic Research, 6: 385–392 (1997).
Lee et al, Plant Molecular Biology, 28: 871–884 (1995).
Li et al, The Journal of Biological Chemistry, 257(9): 6537–6545 (2000).
McGranahan et al, Bio/Technology, 6: 800–804 (1988).
Minocha et al, 1986 Research and Development Conference, Tappi Procedings, 89–92 (1986).
Napoli et al, The Plant Cell, 2: 279–289 (1990).
Ni et al, Transgenic Research, 3: 120–126 (1994).
Ranjeva et al, Biochimie, 58: 1255–1262 (1976).
Smith et al, Nature, 334: 724–726 (1988).
Sullivan et al, Plant Cell Reports, 12: 303–306 (1993).
Tsai et al, Plant Cell Reports, 14: 94–97 (1994).
Van Doorsselaere et al, The Plant Journal, 8(6): 855–864 (1995).
Whetten et al, Forest Ecology and Management, 43: 301–316 (1991).
Whetten et al, Annu. Rev. Plan Physiol. Plant Mol. Biol., 49:585–609 (1998).
Wilde et al, Plant Physiol 98: 114–120 (1992).

* cited by examiner

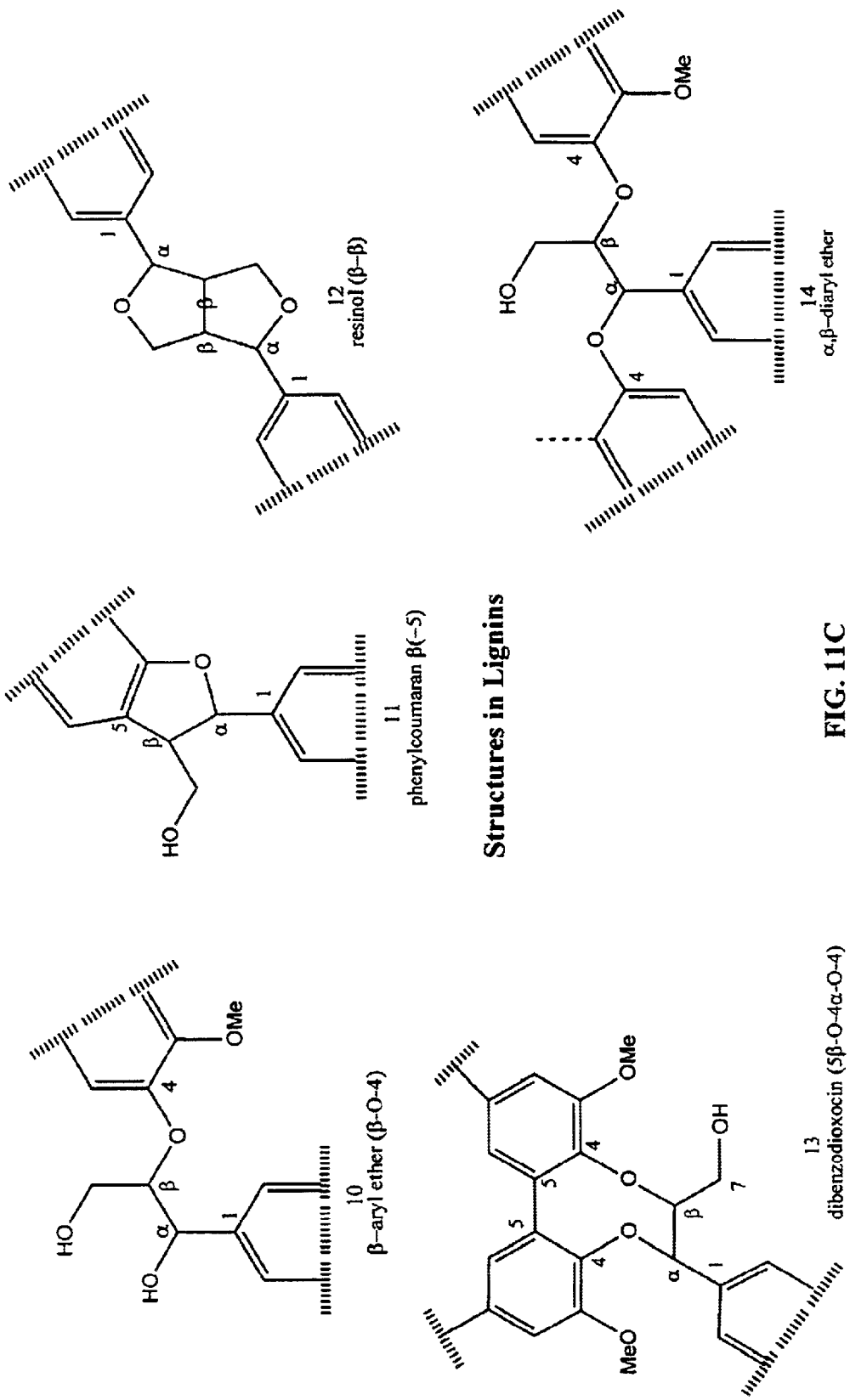
FIG. 11C Structures in Lignins

SEQUENCE LISTING

<160> NUMBER OF SEQ ID NOS: 17

<210> SEQ ID NO 1
<211> LENGTH: 1915
<212> TYPE: DNA
<213> ORGANISM: Populus tremuloides Michx. (aspen)
<220> FEATURE:
<221> NAME/KEY: CDS
<222> LOCATION: (83)...(1687)

<400> SEQUENCE: 1

```
ccctcgcgaa actccgaaaa cagagagcac ctaaaactca ccatctctcc ctctgcatct      60
ttagcccgca atggacgcca ca atg aat cca caa gaa ttc atc ttt cgc tca     112
                         Met Asn Pro Gln Glu Phe Ile Phe Arg Ser
                           1               5                  10 aaa tta cca gac atc tac atc ccg aaa aac ctt ccc ctg cat tca tac      160
Lys Leu Pro Asp Ile Tyr Ile Pro Lys Asn Leu Pro Leu His Ser Tyr
                 15                  20                  25 gtt ctt gag aac ttg tct aaa cat tca tca aaa cct tgc ctg ata aat      208
Val Leu Glu Asn Leu Ser Lys His Ser Ser Lys Pro Cys Leu Ile Asn
         30                  35                  40 ggc gcg aat gga gat gtc tac acc tat gct gat gtt gag ctc aca gca      256
Gly Ala Asn Gly Asp Val Tyr Thr Tyr Ala Asp Val Glu Leu Thr Ala
     45                  50                  55 aga aga gtt gct tct ggt ctg aac aag att ggt att caa caa ggt gac      304
Arg Arg Val Ala Ser Gly Leu Asn Lys Ile Gly Ile Gln Gln Gly Asp
```

-continued

|     |     |
| --- | --- |
| gtg atc atg ctc ttc cta cca agt tca cct gaa ttc gtg ctt gct ttc<br>Val Ile Met Leu Phe Leu Pro Ser Ser Pro Glu Phe Val Leu Ala Phe<br>75                              80                              85                              90 | 352 |
| cta ggc gct tca cac aga ggt gcc atg atc act gct gcc aat cct ttc<br>Leu Gly Ala Ser His Arg Gly Ala Met Ile Thr Ala Ala Asn Pro Phe<br>                              95                              100                              105 | 400 |
| tcc acc cct gca gag cta gca aaa cat gcc aag gcc tcg aga gca aag<br>Ser Thr Pro Ala Glu Leu Ala Lys His Ala Lys Ala Ser Arg Ala Lys<br>                      110                              115                              120 | 448 |
| ctt ctg ata aca cag gct tgt tac tac gag aag gtt aaa gat ttt gcc<br>Leu Leu Ile Thr Gln Ala Cys Tyr Tyr Glu Lys Val Lys Asp Phe Ala<br>125                             130                              135 | 496 |
| cga gaa agt gat gtt aag gtc atg tgc gtg gac tct gcc ccg gac ggt<br>Arg Glu Ser Asp Val Lys Val Met Cys Val Asp Ser Ala Pro Asp Gly<br>                      140                              145                              150 | 544 |
| gct tca ctt ttc aga gct cac aca cag gca gac gaa aat gaa gtg cct<br>Ala Ser Leu Phe Arg Ala His Thr Gln Ala Asp Glu Asn Glu Val Pro<br>155                             160                              165                              170 | 592 |
| cag gtc gac att agt cct gat gat gtc gta gca ttg cct tat tca tca<br>Gln Val Asp Ile Ser Pro Asp Asp Val Val Ala Leu Pro Tyr Ser Ser<br>                      175                              180                              185 | 640 |
| ggg act aca ggg ttg cca aaa ggg gtc atg tta acg cac aaa ggg cta<br>Gly Thr Thr Gly Leu Pro Lys Gly Val Met Leu Thr His Lys Gly Leu<br>                      190                              195                              200 | 688 |
| ata acc agt gtg gct caa cag gta gat gga gac aat cct aac ctg tat<br>Ile Thr Ser Val Ala Gln Gln Val Asp Gly Asp Asn Pro Asn Leu Tyr<br>                      205                              210                              215 | 736 |
| ttt cac agt gaa gat gtg att ctg tgt gtg ctt cct atg ttc cat atc<br>Phe His Ser Glu Asp Val Ile Leu Cys Val Leu Pro Met Phe His Ile<br>220                             225                              230 | 784 |
| tat gct ctg aat tca atg atg ctc tgt ggt ctg aga gtt ggt gcc tcg<br>Tyr Ala Leu Asn Ser Met Met Leu Cys Gly Leu Arg Val Gly Ala Ser<br>235                             240                             245                              250 | 832 |
| att ttg ata atg cca aag ttt gag att ggt tct ttg ctg gga ttg att<br>Ile Leu Ile Met Pro Lys Phe Glu Ile Gly Ser Leu Leu Gly Leu Ile<br>                              255                              260                              265 | 880 |
| gag aag tac aag gta tct ata gca cca gtt gtt cca cct gtg atg atg<br>Glu Lys Tyr Lys Val Ser Ile Ala Pro Val Val Pro Pro Val Met Met<br>                      270                              275                              280 | 928 |
| gca att gct aag tca cct gat ctt gac aag cat gac ctg tct tct ttg<br>Ala Ile Ala Lys Ser Pro Asp Leu Asp Lys His Asp Leu Ser Ser Leu<br>                              285                              290                              295 | 976 |
| agg atg ata aaa tct gga ggg gct cca ttg ggc aag gaa ctt gaa gat<br>Arg Met Ile Lys Ser Gly Gly Ala Pro Leu Gly Lys Glu Leu Glu Asp<br>300                             305                              310 | 1024 |
| act gtc aga gct aag ttt cct cag gct aga ctt ggt cag gga tat gga<br>Thr Val Arg Ala Lys Phe Pro Gln Ala Arg Leu Gly Gln Gly Tyr Gly<br>315                             320                              325                              330 | 1072 |
| atg acc gag gca gga cct gtt cta gca atg tgc ttg gca ttt gcc aag<br>Met Thr Glu Ala Gly Pro Val Leu Ala Met Cys Leu Ala Phe Ala Lys<br>                              335                              340                              345 | 1120 |
| gaa cca ttc gac ata aaa cca ggt gca tgt gga act gta gtc agg aat<br>Glu Pro Phe Asp Ile Lys Pro Gly Ala Cys Gly Thr Val Val Arg Asn<br>                      350                              355                              360 | 1168 |
| gca gag atg aag att gtt gac cca gaa aca ggg gtc tct cta ccg agg<br>Ala Glu Met Lys Ile Val Asp Pro Glu Thr Gly Val Ser Leu Pro Arg<br>365                             370                             375 | 1216 |
| aac cag cct ggt gag atc tgc atc cgg ggt gat cag atc atg aaa gga | 1264 |

```
Asn Gln Pro Gly Glu Ile Cys Ile Arg Gly Asp Gln Ile Met Lys Gly
    380                 385                 390 tat ctt aat gac ccc gag gca acc tca aga aca ata gac aaa gaa gga      1312
Tyr Leu Asn Asp Pro Glu Ala Thr Ser Arg Thr Ile Asp Lys Glu Gly
395                 400                 405                 410 tgg ctg cac aca ggc gat atc ggc tac att gat gat gat gat gag ctt      1360
Trp Leu His Thr Gly Asp Ile Gly Tyr Ile Asp Asp Asp Asp Glu Leu
                415                 420                 425 ttc atc gtt gac aga ttg aag gaa ttg atc aag tat aaa ggg ttt cag      1408
Phe Ile Val Asp Arg Leu Lys Glu Leu Ile Lys Tyr Lys Gly Phe Gln
            430                 435                 440 gtt gct cct act gaa ctc gaa gct ttg tta ata gcc cat cca gag ata      1456
Val Ala Pro Thr Glu Leu Glu Ala Leu Leu Ile Ala His Pro Glu Ile
        445                 450                 455 tcc gat gct gct gta gta gga ttg aaa gat gag gat gcg gga gaa gtt      1504
Ser Asp Ala Ala Val Val Gly Leu Lys Asp Glu Asp Ala Gly Glu Val
    460                 465                 470 cct gtt gca ttt gta gtg aaa tca gaa aag tct cag gcc acc gaa gat      1552
Pro Val Ala Phe Val Val Lys Ser Glu Lys Ser Gln Ala Thr Glu Asp
475                 480                 485                 490 gaa att aag cag tat att tca aaa cag gtg atc ttc tac aag aga ata      1600
Glu Ile Lys Gln Tyr Ile Ser Lys Gln Val Ile Phe Tyr Lys Arg Ile
                495                 500                 505 aaa cga gtt ttc ttc att gaa gca att ccc aag gca cca tca ggc aag      1648
Lys Arg Val Phe Phe Ile Glu Ala Ile Pro Lys Ala Pro Ser Gly Lys
            510                 515                 520 atc ctg agg aag aat ctg aaa gag aag ttg cca ggc ata taactgaaga       1697
Ile Leu Arg Lys Asn Leu Lys Glu Lys Leu Pro Gly Ile
        525                 530                 535 tgttactgaa catttaaccc tctgtcttat ttctttaata cttgcgaatc attgtagtgt    1757
tgaaccaagc atgcttggaa aagacacgta cccaacgtaa gacagttact gttcctagta    1817
tacaagctct ttaatgttcg ttttgaactt gggaaaacat aagttctcct gtcgccatat    1877
ggagtaattc aattgaatat tttggtttct ttaatgat                            1915
```

<210> SEQ ID NO 2
<211> LENGTH: 535
<212> TYPE: PRT
<213> ORGANISM: Populus tremuloides Michx. (aspen)

<400> SEQUENCE: 2

```
Met Asn Pro Gln Glu Phe Ile Phe Arg Ser Lys Leu Pro Asp Ile Tyr
1               5                   10                  15

Ile Pro Lys Asn Leu Pro Leu His Ser Tyr Val Leu Glu Asn Leu Ser
                20                  25                  30

Lys His Ser Ser Lys Pro Cys Leu Ile Asn Gly Ala Asn Gly Asp Val
            35                  40                  45

Tyr Thr Tyr Ala Asp Val Glu Leu Thr Ala Arg Arg Val Ala Ser Gly
        50                  55                  60

Leu Asn Lys Ile Gly Ile Gln Gln Gly Asp Val Ile Met Leu Phe Leu
65                  70                  75                  80

Pro Ser Ser Pro Glu Phe Val Leu Ala Phe Leu Gly Ala Ser His Arg
                85                  90                  95

Gly Ala Met Ile Thr Ala Ala Asn Pro Phe Ser Thr Pro Ala Glu Leu
            100                 105                 110

Ala Lys His Ala Lys Ala Ser Arg Ala Lys Leu Leu Ile Thr Gln Ala
        115                 120                 125
```

-continued

```
Cys Tyr Tyr Glu Lys Val Lys Asp Phe Ala Arg Glu Ser Asp Val Lys
    130                 135                 140

Val Met Cys Val Asp Ser Ala Pro Asp Gly Ala Ser Leu Phe Arg Ala
145                 150                 155                 160

His Thr Gln Ala Asp Glu Asn Glu Val Pro Gln Val Asp Ile Ser Pro
                165                 170                 175

Asp Asp Val Val Ala Leu Pro Tyr Ser Ser Gly Thr Thr Gly Leu Pro
            180                 185                 190

Lys Gly Val Met Leu Thr His Lys Gly Leu Ile Thr Ser Val Ala Gln
        195                 200                 205

Gln Val Asp Gly Asp Asn Pro Asn Leu Tyr Phe His Ser Glu Asp Val
    210                 215                 220

Ile Leu Cys Val Leu Pro Met Phe His Ile Tyr Ala Leu Asn Ser Met
225                 230                 235                 240

Met Leu Cys Gly Leu Arg Val Gly Ala Ser Ile Leu Ile Met Pro Lys
                245                 250                 255

Phe Glu Ile Gly Ser Leu Leu Gly Leu Ile Glu Lys Tyr Lys Val Ser
            260                 265                 270

Ile Ala Pro Val Val Pro Pro Val Met Met Ala Ile Ala Lys Ser Pro
        275                 280                 285

Asp Leu Asp Lys His Asp Leu Ser Ser Leu Arg Met Ile Lys Ser Gly
    290                 295                 300

Gly Ala Pro Leu Gly Lys Glu Leu Glu Asp Thr Val Arg Ala Lys Phe
305                 310                 315                 320

Pro Gln Ala Arg Leu Gly Gln Gly Tyr Gly Met Thr Glu Ala Gly Pro
                325                 330                 335

Val Leu Ala Met Cys Leu Ala Phe Ala Lys Glu Pro Phe Asp Ile Lys
            340                 345                 350

Pro Gly Ala Cys Gly Thr Val Val Arg Asn Ala Glu Met Lys Ile Val
        355                 360                 365

Asp Pro Glu Thr Gly Val Ser Leu Pro Arg Asn Gln Pro Gly Glu Ile
    370                 375                 380

Cys Ile Arg Gly Asp Gln Ile Met Lys Gly Tyr Leu Asn Asp Pro Glu
385                 390                 395                 400

Ala Thr Ser Arg Thr Ile Asp Lys Glu Gly Trp Leu His Thr Gly Asp
                405                 410                 415

Ile Gly Tyr Ile Asp Asp Asp Glu Leu Phe Ile Val Asp Arg Leu
            420                 425                 430

Lys Glu Leu Ile Lys Tyr Lys Gly Phe Gln Val Ala Pro Thr Glu Leu
        435                 440                 445

Glu Ala Leu Leu Ile Ala His Pro Glu Ile Ser Asp Ala Ala Val Val
    450                 455                 460

Gly Leu Lys Asp Glu Asp Ala Gly Glu Val Pro Val Ala Phe Val Val
465                 470                 475                 480

Lys Ser Glu Lys Ser Gln Ala Thr Glu Asp Glu Ile Lys Gln Tyr Ile
                485                 490                 495

Ser Lys Gln Val Ile Phe Tyr Lys Arg Ile Lys Arg Val Phe Phe Ile
            500                 505                 510

Glu Ala Ile Pro Lys Ala Pro Ser Gly Lys Ile Leu Arg Lys Asn Leu
        515                 520                 525

Lys Glu Lys Leu Pro Gly Ile
    530                 535
```

-continued

<210> SEQ ID NO 3
<211> LENGTH: 1710
<212> TYPE: DNA
<213> ORGANISM: Populus tremuloides Michx. (aspen)
<220> FEATURE:
<221> NAME/KEY: CDS
<222> LOCATION: (1)...(1710)

<400> SEQUENCE: 3

| | | | | | | | | | | | | | | | | |
|---|---|---|---|---|---|---|---|---|---|---|---|---|---|---|---|---|
| atg | atg | tcc | gtg | gcc | acg | gtt | gag | ccc | ccg | aaa | ccg | gaa | ctc | tcc | cct | 48 |
| Met | Met | Ser | Val | Ala | Thr | Val | Glu | Pro | Pro | Lys | Pro | Glu | Leu | Ser | Pro | |
| 1 | | | | 5 | | | | | 10 | | | | | 15 | | |
| cca | caa | aac | caa | aac | gca | cca | tcc | tct | cat | gaa | act | gat | cac | att | ttc | 96 |
| Pro | Gln | Asn | Gln | Asn | Ala | Pro | Ser | Ser | His | Glu | Thr | Asp | His | Ile | Phe | |
| | | 20 | | | | | 25 | | | | | 30 | | | | |
| aga | tca | aaa | cta | cca | gac | ata | acc | atc | tcg | aac | gac | ctc | cct | ctg | cac | 144 |
| Arg | Ser | Lys | Leu | Pro | Asp | Ile | Thr | Ile | Ser | Asn | Asp | Leu | Pro | Leu | His | |
| | 35 | | | | | 40 | | | | | 45 | | | | | |
| gca | tac | tgc | ttt | gaa | aac | ctc | tct | gat | ttc | tca | gat | agg | cca | tgc | ttg | 192 |
| Ala | Tyr | Cys | Phe | Glu | Asn | Leu | Ser | Asp | Phe | Ser | Asp | Arg | Pro | Cys | Leu | |
| 50 | | | | | 55 | | | | | 60 | | | | | | |
| att | tca | ggt | tcc | acg | gga | aaa | acc | tat | tct | ttt | gcc | gaa | act | cac | ctc | 240 |
| Ile | Ser | Gly | Ser | Thr | Gly | Lys | Thr | Tyr | Ser | Phe | Ala | Glu | Thr | His | Leu | |
| 65 | | | | | 70 | | | | | 75 | | | | | 80 | |
| ata | tct | cgg | aag | gtc | gct | gct | ggg | tta | tcc | aat | ttg | ggc | atc | aag | aaa | 288 |
| Ile | Ser | Arg | Lys | Val | Ala | Ala | Gly | Leu | Ser | Asn | Leu | Gly | Ile | Lys | Lys | |
| | | | 85 | | | | | 90 | | | | | 95 | | | |
| ggc | gat | gta | atc | atg | acc | ctg | ctc | caa | aac | tgc | cca | gaa | ttc | gtc | ttc | 336 |
| Gly | Asp | Val | Ile | Met | Thr | Leu | Leu | Gln | Asn | Cys | Pro | Glu | Phe | Val | Phe | |
| | | | | 100 | | | | | 105 | | | | | 110 | | |
| tcc | ttc | atc | ggt | gct | tcc | atg | att | ggt | gca | gtc | atc | acc | act | gcg | aac | 384 |
| Ser | Phe | Ile | Gly | Ala | Ser | Met | Ile | Gly | Ala | Val | Ile | Thr | Thr | Ala | Asn | |
| | | 115 | | | | | 120 | | | | | 125 | | | | |
| cct | ttc | tac | act | caa | agt | gaa | ata | ttc | aag | caa | ttc | tct | gct | tct | cgt | 432 |
| Pro | Phe | Tyr | Thr | Gln | Ser | Glu | Ile | Phe | Lys | Gln | Phe | Ser | Ala | Ser | Arg | |
| | 130 | | | | | 135 | | | | | 140 | | | | | |
| gcg | aaa | ctg | att | atc | acc | cag | tct | caa | tat | gtg | aac | aag | cta | gga | gat | 480 |
| Ala | Lys | Leu | Ile | Ile | Thr | Gln | Ser | Gln | Tyr | Val | Asn | Lys | Leu | Gly | Asp | |
| 145 | | | | | 150 | | | | | 155 | | | | | 160 | |
| agt | gat | tgc | cat | gaa | aac | aac | caa | aaa | ccg | ggg | gaa | gat | ttc | ata | gta | 528 |
| Ser | Asp | Cys | His | Glu | Asn | Asn | Gln | Lys | Pro | Gly | Glu | Asp | Phe | Ile | Val | |
| | | | | 165 | | | | | 170 | | | | | 175 | | |
| atc | acc | att | gat | gac | ccg | cca | gag | aac | tgt | cta | cat | ttc | aat | gtg | ctt | 576 |
| Ile | Thr | Ile | Asp | Asp | Pro | Pro | Glu | Asn | Cys | Leu | His | Phe | Asn | Val | Leu | |
| | | | 180 | | | | | 185 | | | | | 190 | | | |
| gtc | gag | gct | agc | gag | agt | gaa | atg | cca | aca | gtt | tca | atc | ctt | ccg | gat | 624 |
| Val | Glu | Ala | Ser | Glu | Ser | Glu | Met | Pro | Thr | Val | Ser | Ile | Leu | Pro | Asp | |
| | | 195 | | | | | 200 | | | | | 205 | | | | |
| gat | cct | gtg | gca | tta | cca | ttc | tct | tca | ggg | aca | aca | ggg | ctc | cca | aaa | 672 |
| Asp | Pro | Val | Ala | Leu | Pro | Phe | Ser | Ser | Gly | Thr | Thr | Gly | Leu | Pro | Lys | |
| | 210 | | | | | 215 | | | | | 220 | | | | | |
| gga | gtg | ata | ctg | acc | cac | aag | agc | ttg | ata | aca | agt | gtg | gct | caa | caa | 720 |
| Gly | Val | Ile | Leu | Thr | His | Lys | Ser | Leu | Ile | Thr | Ser | Val | Ala | Gln | Gln | |
| 225 | | | | | 230 | | | | | 235 | | | | | 240 | |
| gtt | gat | gga | gag | atc | cca | aat | tta | tac | ttg | aaa | caa | gat | gac | gtt | gtt | 768 |
| Val | Asp | Gly | Glu | Ile | Pro | Asn | Leu | Tyr | Leu | Lys | Gln | Asp | Asp | Val | Val | |
| | | | | 245 | | | | | 250 | | | | | 255 | | |
| tta | tgc | gtt | tta | cct | ttg | ttt | cac | atc | ttt | tca | ttg | aac | agc | gtg | ttg | 816 |
| Leu | Cys | Val | Leu | Pro | Leu | Phe | His | Ile | Phe | Ser | Leu | Asn | Ser | Val | Leu | |
| | | | | 260 | | | | | 265 | | | | | 270 | | |
| tta | tgc | tcg | ttg | aga | gcc | ggt | tct | gct | gtt | ctt | tta | atg | caa | aag | ttt | 864 |

```
Leu Cys Ser Leu Arg Ala Gly Ser Ala Val Leu Leu Met Gln Lys Phe
            275                 280                 285 gag ata gga tca ctg cta gag ctc att cag aaa cac aat gtt tcg gtt        912
Glu Ile Gly Ser Leu Leu Glu Leu Ile Gln Lys His Asn Val Ser Val
        290                 295                 300 gcg gct gtg gtg cca cca ctg gtg ctg gcg ttg gcc aag aac cca ttg        960
Ala Ala Val Val Pro Pro Leu Val Leu Ala Leu Ala Lys Asn Pro Leu
305                 310                 315                 320 gag gcg aac ttc gac ttg agt tcg atc agg gta gtc ctg tca ggg gct       1008
Glu Ala Asn Phe Asp Leu Ser Ser Ile Arg Val Val Leu Ser Gly Ala
                325                 330                 335 gcg cca ctg ggg aag gag ctc gag gac gcc ctc agg agc agg gtt cct       1056
Ala Pro Leu Gly Lys Glu Leu Glu Asp Ala Leu Arg Ser Arg Val Pro
            340                 345                 350 cag gcc atc ctg gga cag ggt tat ggg atg aca gag gcc ggg cct gtg       1104
Gln Ala Ile Leu Gly Gln Gly Tyr Gly Met Thr Glu Ala Gly Pro Val
        355                 360                 365 cta tca atg tgc tta gcc ttt tca aag caa cct ttc cca acc aag tct       1152
Leu Ser Met Cys Leu Ala Phe Ser Lys Gln Pro Phe Pro Thr Lys Ser
    370                 375                 380 ggg tcg tgt gga acg gtg gtt aga aac gca gag ctc aag gtc att gac       1200
Gly Ser Cys Gly Thr Val Val Arg Asn Ala Glu Leu Lys Val Ile Asp
385                 390                 395                 400 cct gag acc ggt cgc tct ctt ggt tac aac caa cct ggt gaa atc tgc       1248
Pro Glu Thr Gly Arg Ser Leu Gly Tyr Asn Gln Pro Gly Glu Ile Cys
                405                 410                 415 atc cgt gga tcc caa atc atg aaa gga tat ttg aat gac gcg gaa gcc       1296
Ile Arg Gly Ser Gln Ile Met Lys Gly Tyr Leu Asn Asp Ala Glu Ala
            420                 425                 430 acg gca aac acc ata gac gtt gag ggt tgg ctc cac act gga gat ata       1344
Thr Ala Asn Thr Ile Asp Val Glu Gly Trp Leu His Thr Gly Asp Ile
        435                 440                 445 ggt tat gtc gac gac gac gac gag att ttc att gtt gat aga gtg aag       1392
Gly Tyr Val Asp Asp Asp Asp Glu Ile Phe Ile Val Asp Arg Val Lys
    450                 455                 460 gaa atc ata aaa ttc aaa ggc ttc cag gtg ccg cca gcg gag ctt gag       1440
Glu Ile Ile Lys Phe Lys Gly Phe Gln Val Pro Pro Ala Glu Leu Glu
465                 470                 475                 480 gct ctc ctt gta aac cac cct tca att gcg gat gcg gct gtt gtt ccg       1488
Ala Leu Leu Val Asn His Pro Ser Ile Ala Asp Ala Ala Val Val Pro
                485                 490                 495 caa aaa gac gag gtt gct ggt gaa gtt cct gtc gcg ttt gtg gtc cgc       1536
Gln Lys Asp Glu Val Ala Gly Glu Val Pro Val Ala Phe Val Val Arg
            500                 505                 510 tca gat gat ctt gac ctt agt gaa gag gct gta aaa gaa tac att gca       1584
Ser Asp Asp Leu Asp Leu Ser Glu Glu Ala Val Lys Glu Tyr Ile Ala
        515                 520                 525 aag cag gtg gtg ttc tac aag aaa ctg cac aag gtg ttc ttc gtt cat       1632
Lys Gln Val Val Phe Tyr Lys Lys Leu His Lys Val Phe Phe Val His
    530                 535                 540 tct att ccc aaa tcg gct tct gga aag att cta aga aaa gac ctc aga       1680
Ser Ile Pro Lys Ser Ala Ser Gly Lys Ile Leu Arg Lys Asp Leu Arg
545                 550                 555                 560 gcc aag ctt gcc aca gcc acc acc atg tcc                               1710
Ala Lys Leu Ala Thr Ala Thr Thr Met Ser
                565                 570

<210> SEQ ID NO 4
<211> LENGTH: 570
<212> TYPE: PRT
```

<213> ORGANISM: Populus tremuloides Michx. (aspen)

<400> SEQUENCE: 4

```
Met Met Ser Val Ala Thr Val Glu Pro Pro Lys Pro Glu Leu Ser Pro
 1               5                  10                  15
Pro Gln Asn Gln Asn Ala Pro Ser Ser His Glu Thr Asp His Ile Phe
            20                  25                  30
Arg Ser Lys Leu Pro Asp Ile Thr Ile Ser Asn Asp Leu Pro Leu His
        35                  40                  45
Ala Tyr Cys Phe Glu Asn Leu Ser Asp Phe Ser Asp Arg Pro Cys Leu
    50                  55                  60
Ile Ser Gly Ser Thr Gly Lys Thr Tyr Ser Phe Ala Glu Thr His Leu
65                  70                  75                  80
Ile Ser Arg Lys Val Ala Ala Gly Leu Ser Asn Leu Gly Ile Lys Lys
                85                  90                  95
Gly Asp Val Ile Met Thr Leu Leu Gln Asn Cys Pro Glu Phe Val Phe
            100                 105                 110
Ser Phe Ile Gly Ala Ser Met Ile Gly Ala Val Ile Thr Thr Ala Asn
        115                 120                 125
Pro Phe Tyr Thr Gln Ser Glu Ile Phe Lys Gln Phe Ser Ala Ser Arg
    130                 135                 140
Ala Lys Leu Ile Ile Thr Gln Ser Gln Tyr Val Asn Lys Leu Gly Asp
145                 150                 155                 160
Ser Asp Cys His Glu Asn Asn Gln Lys Pro Gly Glu Asp Phe Ile Val
                165                 170                 175
Ile Thr Ile Asp Asp Pro Pro Glu Asn Cys Leu His Phe Asn Val Leu
            180                 185                 190
Val Glu Ala Ser Glu Ser Glu Met Pro Thr Val Ser Ile Leu Pro Asp
        195                 200                 205
Asp Pro Val Ala Leu Pro Phe Ser Ser Gly Thr Thr Gly Leu Pro Lys
210                 215                 220
Gly Val Ile Leu Thr His Lys Ser Leu Ile Thr Ser Val Ala Gln Gln
225                 230                 235                 240
Val Asp Gly Glu Ile Pro Asn Leu Tyr Leu Lys Gln Asp Asp Val Val
                245                 250                 255
Leu Cys Val Leu Pro Leu Phe His Ile Phe Ser Leu Asn Ser Val Leu
            260                 265                 270
Leu Cys Ser Leu Arg Ala Gly Ser Ala Val Leu Leu Met Gln Lys Phe
        275                 280                 285
Glu Ile Gly Ser Leu Leu Glu Leu Ile Gln Lys His Asn Val Ser Val
    290                 295                 300
Ala Ala Val Val Pro Pro Leu Val Leu Ala Leu Ala Lys Asn Pro Leu
305                 310                 315                 320
Glu Ala Asn Phe Asp Leu Ser Ser Ile Arg Val Val Leu Ser Gly Ala
                325                 330                 335
Ala Pro Leu Gly Lys Glu Leu Glu Asp Ala Leu Arg Ser Arg Val Pro
            340                 345                 350
Gln Ala Ile Leu Gly Gln Gly Tyr Gly Met Thr Glu Ala Gly Pro Val
        355                 360                 365
Leu Ser Met Cys Leu Ala Phe Ser Lys Gln Pro Phe Pro Thr Lys Ser
    370                 375                 380
Gly Ser Cys Gly Thr Val Val Arg Asn Ala Glu Leu Lys Val Ile Asp
385                 390                 395                 400
```

-continued

```
Pro Glu Thr Gly Arg Ser Leu Gly Tyr Asn Gln Pro Gly Glu Ile Cys
                405                 410                 415
Ile Arg Gly Ser Gln Ile Met Lys Gly Tyr Leu Asn Asp Ala Glu Ala
            420                 425                 430
Thr Ala Asn Thr Ile Asp Val Glu Gly Trp Leu His Thr Gly Asp Ile
        435                 440                 445
Gly Tyr Val Asp Asp Asp Glu Ile Phe Ile Val Asp Arg Val Lys
    450                 455                 460
Glu Ile Ile Lys Phe Lys Gly Phe Gln Val Pro Pro Ala Glu Leu Glu
465                 470                 475                 480
Ala Leu Leu Val Asn His Pro Ser Ile Ala Asp Ala Val Val Pro
                485                 490                 495
Gln Lys Asp Glu Val Ala Gly Val Pro Val Ala Phe Val Val Arg
            500                 505                 510
Ser Asp Asp Leu Asp Leu Ser Glu Glu Ala Val Lys Glu Tyr Ile Ala
        515                 520                 525
Lys Gln Val Phe Tyr Lys Lys Leu His Lys Val Phe Phe Val His
    530                 535                 540
Ser Ile Pro Lys Ser Ala Ser Gly Lys Ile Leu Arg Lys Asp Leu Arg
545                 550                 555                 560
Ala Lys Leu Ala Thr Ala Thr Thr Met Ser
                565                 570
```

<210> SEQ ID NO 5
<211> LENGTH: 1172
<212> TYPE: DNA
<213> ORGANISM: Populus tremuloides Michx. (aspen)

<400> SEQUENCE: 5

```
tgtaggattg gtggaatggg atcattccta atcccttaat gacggtggca tgaacacaaa      60
gcaaagagaa gttaggtcac tcctccttta tatatatata tatatgcatg catgaggacc     120
atggctatga tgaaggttaa tagaggtagt tgtgattgag atatgtccag cactagtttt     180
ttgttggtgt gatttctcat gatgacgcga aaattttata tatatatata atgaataata     240
tgattgatta ttctctgtaa ttttgtgaaa tagattaaaa cagctcaatg tgaggtgacc     300
agttgtcaaa tgaccactcg acttggggca tggtgatttt tcaaatcaca actcaatttg     360
aaaactaaaa ttaaaaaga tttagattat taaattatta ggttaattca cgggttggct     420
aatcaattat tattaattaa aacgatagta tttttgataa tttaattaaa attttattgg     480
atttgaatga actcaattac atcacaaaaa acctaatcaa attaatatct tatgtgatat     540
aatttagaaa tataaatgat taacctttaa atctcgagtt tctcttataa aaaacacgta     600
taattgggct agatttaaca gctattattc aaactggcca ggacaattat taaaattaat     660
aattattatt ttttctaata aagcacttcc taattgttaa aatatatgtc taaacactaa     720
taataaaatt tatttgtgta tctttggcag taggtgagag gtgctgacaa ataaattagt     780
gcataaaata taatggattg gtggtctgtg aaaagacagg tggaggacaa gccacctctc     840
tcaagtcaaa aggccatttc acaaccaacc caaatgggaa cccaccaccg ttccccgcca     900
ttaaaatccc taatctcacc aacccaactc cacagattct tcaccaaacg caactgattt     960
ttcaatcaat gttttcccta tactaccccc ccaacaactc cataataccc aatttgtcct    1020
ttcaccaacc cccgtcctcc gtgccagcca attctatatc agcaggaatg ctctgcactc    1080
tgctttctca ggtctcctac cataagaaaa cagagagcac ctaaaactcg ccatctctcc    1140
```

```
ctctgcatct ttagcccgca atggacgcga ca                                    1172
```

<210> SEQ ID NO 6
<211> LENGTH: 1180
<212> TYPE: DNA
<213> ORGANISM: Populus tremuloides Michx. (aspen)

<400> SEQUENCE: 6

```
aagctttgag tattcatatg ggtattcatc cgaccattat ttttcaattt gtgttgtgtt        60
gatccaattt tcaacttatt ttttttttcac ttatttttta ttagttattt ttattttttat     120
tatttttta  aaaatttaaa aattaaatta taacatttt  attttatccc tcattaacta       180
aaatagggat ggtaatagat attcatgaag ggagttatat atcaaatgat attagttaag       240
ctattttgat atttataccc tactcattac ttatggaata aaaaatttag atatttataa       300
aatatttatc ggatttcagg tattcatatg aatatttatt tgattattat ttattcaaca       360
aaaaataaaa caattaatat gcatgtttga agtttatata tatattaagt taggtttaga       420
tagattttgg gtggggttaa ttaatattca taccctatct actatctatc aaataatcca       480
aataaattca cctaaattag gttgggtttg tattcatcaa gttaacatta aattgtaatt       540
ccgtaagtaa ctaaacaagt acaaagactt ctattttatc ttatatatta ccataaagcc       600
aactatattt cctattcttt ttcatccctt ctatcgtaat tttctgtgac ttttttattt       660
atatattaac ggtaacgaaa cacagcaata aaagttattg tgaaagatat ggataattat       720
tatggtgact atgaaagagt aaatttgcca tgcactaagt tcctagtgtc atctcataaa       780
agacttgtct gccacgtaag ctgttgtgag tgtcgtttat ttacgcgtgt caaccaatcg       840
ctgccaattg actcttgagg gtaggtgaga gcttcggctt tgatgggaac tgcatgaggc       900
ataggggttg gtttcttgaa tgtgagatgg gcatgctttg gctcccttgc tactcacctc       960
atcttcaatt tgccagctca gctaccagtc tctcaccact agtttcacca aactttctct      1020
gctcctgtat ttattacacc ttgctcgatt ggctccgtcc tcgtacacgc atccacaccg      1080
atcgatcgat tagaaccata cagaattggg attggttggg tttacattct gcgttagata      1140
catctatcac agaaagaaac tcccttccat ctcaggaaac                            1180
```

<210> SEQ ID NO 7
<211> LENGTH: 12
<212> TYPE: PRT
<213> ORGANISM: Populus tremuloides Michx. (aspen)

<400> SEQUENCE: 7

Leu Pro Tyr Ser Ser Gly Thr Thr Gly Leu Pro Lys
 1               5                  10

<210> SEQ ID NO 8
<211> LENGTH: 7
<212> TYPE: PRT
<213> ORGANISM: Populus tremuloides Michx. (aspen)

<400> SEQUENCE: 8

Gly Glu Ile Cys Ile Arg Gly
 1               5

<210> SEQ ID NO 9
<211> LENGTH: 31
<212> TYPE: DNA
<213> ORGANISM: Populus tremuloides Michx. (aspen)
<220> FEATURE:
<221> NAME/KEY: modified_base

```
<222> LOCATION: (11)
<223> OTHER INFORMATION: n represents inosine
<220> FEATURE:
<221> NAME/KEY: modified_base
<222> LOCATION: (14)
<223> OTHER INFORMATION: n represents inosine
<220> FEATURE:
<221> NAME/KEY: modified_base
<222> LOCATION: (17)
<223> OTHER INFORMATION: n represents inosine
<220> FEATURE:
<221> NAME/KEY: modified_base
<222> LOCATION: (20)
<223> OTHER INFORMATION: n represents inosine
<220> FEATURE:
<221> NAME/KEY: modified_base
<222> LOCATION: (23)
<223> OTHER INFORMATION: n represents inosine

<400> SEQUENCE: 9
ttggatccgg nacnacnggn ytnccnaarg g                              31

<210> SEQ ID NO 10
<211> LENGTH: 28
<212> TYPE: DNA
<213> ORGANISM: Populus tremuloides Michx. (aspen)
<220> FEATURE:
<221> NAME/KEY: modified_base
<222> LOCATION: (11)
<223> OTHER INFORMATION: n represents inosine
<220> FEATURE:
<221> NAME/KEY: modified_base
<222> LOCATION: (14)
<223> OTHER INFORMATION: n represents inosine
<220> FEATURE:
<221> NAME/KEY: modified_base
<222> LOCATION: (23)
<223> OTHER INFORMATION: n represents inosine

<400> SEQUENCE: 10
ttggatccgt ngcncarcar gtngaygg                                  28

<210> SEQ ID NO 11
<211> LENGTH: 27
<212> TYPE: DNA
<213> ORGANISM: Populus tremuloides Michx. (aspen)
<220> FEATURE:
<221> NAME/KEY: modified_base
<222> LOCATION: (10)
<223> OTHER INFORMATION: n represents inosine
<220> FEATURE:
<221> NAME/KEY: modified_base
<222> LOCATION: (25)
<223> OTHER INFORMATION: n represents inosine

<400> SEQUENCE: 11
atgtcgaccn ckdatrcada tytcncc                                   27

<210> SEQ ID NO 12
<211> LENGTH: 7
<212> TYPE: PRT
<213> ORGANISM: Populus tremuloides Michx. (aspen) unknown

<400> SEQUENCE: 12

Gly Glu Ile Cys Ile Arg Gly
 1               5

<210> SEQ ID NO 13
<211> LENGTH: 27
<212> TYPE: DNA
<213> ORGANISM: Populus tremuloides Michx. (aspen)
```

```
<400> SEQUENCE: 13
tctgtctaga tgatgtcgtg gccacgg                                                27

<210> SEQ ID NO 14
<211> LENGTH: 26
<212> TYPE: DNA
<213> ORGANISM: Populus tremuloides Michx. (aspen)

<400> SEQUENCE: 14
ttagatctct aggacatggt ggtggc                                                 26

<210> SEQ ID NO 15
<211> LENGTH: 16
<212> TYPE: DNA
<213> ORGANISM: Populus tremuloides Michx. (aspen)

<400> SEQUENCE: 15
cctttcacca acccccc                                                           16

<210> SEQ ID NO 16
<211> LENGTH: 6
<212> TYPE: DNA
<213> ORGANISM: Populus tremuloides Michx. (aspen)

<400> SEQUENCE: 16 ccgttc                                                                        6

<210> SEQ ID NO 17
<211> LENGTH: 11
<212> TYPE: DNA
<213> ORGANISM: Populus tremuloides Michx. (aspen)

<400> SEQUENCE: 17
tctcaccaac c                                                                 11
```

4-COUMARATE CO-ENZYME A LIGASE PROMOTER

CROSS-REFERENCE TO RELATED APPLICATIONS

This application is a 371 of PCT/US98/24138 filed Nov. 12, 1998, which is a continuation-in-part of U.S. application Ser. No. 08/969,046 filed Nov. 12, 1997, now U.S. Pat. No. 6,455,762, the disclosure of which is incorporated by reference herein.

FIELD OF THE INVENTION

The invention relates to genetically modifying plants, e.g., trees, through manipulation of the lignin biosynthesis pathway, and more particularly, to genetically modifying plants through the down regulation of 4-coumarate Co-enzyme A ligase (4CL) to achieve faster growth. Down regulation of 4CL may also achieve altered lignin content, and/or altered lignin structure, and/or altered cellulose content, and/or altered disease resistance of the trees. Moreover, promoters of the 4CL genes are useful to drive gene expression specifically in xylem tissue or specifically in epidermal tissues.

BACKGROUND OF THE INVENTION

Genetic engineering of plants to conform to desired traits has shifted the emphasis in plant improvement away from the traditional breeding programs during the past decade. Although research on genetic engineering of plants has been vigorous, the progress has been slow.

The ability to make plants grow faster continues to be the top objective of many companies worldwide. The ability to genetically increase the optimal growth of plants would be a commercially significant improvement. Faster growing plants could be used by all sectors of the agriculture and forest products industries worldwide.

Lignin, a complex phenolic polymer, is a major component in cell walls of secondary xylem. In general, lignin constitutes 25% of the dry weight of the wood, making it the second most abundant organic compound on earth after cellulose. Although lignin plays an important role in plants, it usually represents an obstacle to utilizing biomass in several applications. For example, in wood pulp production, lignin has to be removed through expensive and polluting processes in order to recover cellulose.

Thus, it is desirable to genetically engineer plants with reduced lignin content and/or altered lignin composition that can be utilized more efficiently. Plants that could be genetically engineered with a reduced amount of lignin would be commercially valuable. These genetically engineered plants would be less expensive to pulp because, in essence, part of the pulping has already been performed due to the reduced amount of lignin. Further, plants with increased cellulose content would also be commercially valuable to the pulp and paper industry.

Disease resistance in plants is also a desirable plant trait. The impact of disease resistance in plants on the economy of plant products industry worldwide is significant.

Thus, what is needed is the identification and characterization of genes useful to enhance plant growth, alter lignin content and/or structure in plants, alter cellulose content in plants, and/or provide or enhance disease resistance of plants.

SUMMARY OF THE INVENTION

The invention provides a method to genetically alter plants through the down regulation (decrease) or inhibition of native (endogenous) 4-coumarate Co-enzyme A ligase (4CL) in that plant. Such down regulation of 4-coumarate Co-enzyme A ligase results in faster growth, and/or reduced lignin content, and/or altered lignin structure, and/or altered cellulose content, and/or altered disease resistance in the genetically altered plant. The invention also provides for genetically engineered plants, e.g., transformed or transgenic plants, which have been altered to down regulate or inhibit native 4-coumarate Co-enzyme A ligase in the plant so as to achieve faster growth, and/or reduced lignin content, and/or altered lignin structure, and/or increased cellulose content, and/or increased disease resistance. Preferred genetically altered plants include trees, e.g., angiosperms or gymnosperms, forage crops, and more preferably a forest tree, e.g., Populus. Preferred angiosperms include, but are not limited to, Populus, Acacia, Sweetgum, yellow poplar, maple and birch, including pure lines and hybrids thereof. Preferred gymosperms include, but are not limited to, Pine, Spruce, Douglas-fir and hemlock.

The invention further provides a transgenic plant, the genome of which is augmented by a recombinant DNA molecule encoding 4-coumarate Co-enzyme A ligase, or a recombinant DNA molecule comprising an antisense 4-coumarate Co-enzyme A ligase gene, or a fragment thereof. The recombinant DNA molecule is expressed so as to down regulate, decrease or inhibit lignin pathway 4-coumarate Co-enzyme A ligase.

The invention also provides an isolated and purified DNA molecule comprising a DNA segment comprising a transcriptional regulatory control to region of a 4-coumarate Co-enzyme A ligase gene. Preferably, the transcriptional regulatory region comprises a promoter. Tissue specific promoters of a 4-coumarate Co-enzyme A ligase gene can be used to manipulate gene expression in target tissue such as xylem and epidermal tissues, as described hereinbelow. Preferably, the promoter is derived from aspen DNA. Therefore, the invention also provides an expression cassette comprising a transcriptional regulatory region of a 4-coumarate co-enzyme A ligase gene, a method of using the region to express a preselected DNA segment in a tissue-specific manner in plant cells, and a transgenic plant comprising the expression cassette.

Also provided is a method to alter, e.g., enhance, plant growth. The method comprises introducing an expression cassette into cells of a plant, e.g., the cells of a tree, so as to yield genetically altered plant cells. The expression cassette comprises a recombinant DNA molecule, segment, or sequence, comprising a 4-coumarate Co-enzyme A ligase gene, or a fragment thereof. Preferably, the 4-coumarate Co-enzyme A ligase gene, or fragment thereof, is in anti-sense orientation. The 4-coumarate Co-enzyme A ligase gene may be a homologous or heterologous 4-coumarate Co-enzyme A ligase gene. The transformed plant cells are regenerated to provide a genetically altered, e.g., transgenic, plant. The recombinant DNA is expressed in the cells of the regenerated, genetically altered plant in an amount that confers enhanced or accelerated growth to the regenerated, genetically altered plant relative to the corresponding non-genetically altered plant. Preferably, the genetically altered plant is a tree. It is preferred that a genetically altered tree of the invention has an increase in height, leaf size, diameter and/or average internode length relative to the corresponding non-genetically altered tree.

Hence, the invention also provides for a genetically altered plant, the genome of which is augmented by a recombinant DNA molecule encoding 4-coumarate Co-enzyme A ligase, or a recombinant DNA molecule comprising an antisense 4-coumarate Co-enzyme A ligase gene, or fragment thereof, which plant has altered growth characteristics relative to the corresponding non-genetically altered plant.

Further provided is a method to genetically alter plants so as to change or alter their lignin structure. The method comprises introducing an expression cassette into cells of a plant, e.g., a tree, so as to yield genetically altered plant cells. The expression cassette preferably comprises an antisense recombinant DNA molecule, segment or sequence comprising a 4-coumarate Co-enzyme A ligase gene, or a fragment thereof. The transformed plant cells are regenerated to provide a regenerated, genetically altered plant. The recombinant DNA is expressed in the cells of the regenerated, genetically altered plant in an amount that alters the lignin structure in the cells of the plant relative to the corresponding non-genetically altered plant.

Also provided is a method for altering the lignin content in a plant. The method comprises introducing an expression cassette comprising a recombinant DNA molecule comprising a 4-coumarate Co-enzyme A ligase gene operably linked to a promoter functional in a plant cell into the cells of a plant. The plant cells are regenerated so as to yield a genetically altered plant. The recombinant DNA molecule is expressed in the cells of the regenerated plant in an amount effective to alter the lignin content in the plant cells. Preferably, the lignin content is reduced. Also preferably, the lignin content is reduced in a tissue-specific manner. In particular, a reduction in lignin content in forage crops is useful as the digestability of these crops by ruminants is increased. Also preferably, the 4-coumarate Co-enzyme A ligase gene is in an antisense orientation relative to the promoter.

Further provided is a genetically altered, e.g., transgenic, plant having an altered lignin content in the plant cells. The plant comprises a recombinant DNA molecule comprising a nucleotide sequence encoding a plant 4-coumarate Co-enzyme A ligase operably linked to a promoter so that the recombinant DNA molecule is expressed in an amount effective to alter the lignin content of the plant.

Yet another embodiment of the invention is a method to alter, e.g., increase, the cellulose content in plants. The method comprises introducing an expression cassette into cells of a plant, e.g., a tree, so as to yield genetically altered plant cells. The expression cassette preferably comprises an antisense recombinant DNA molecule, segment or sequence comprising a 4-coumarate Co-enzyme A ligase gene, or a fragment thereof, operably linked to a promoter functional in a plant cell. The transformed plant cells are regenerated to provide a regenerated, genetically altered plant. The recombinant DNA is expressed in the cells of the regenerated, genetically altered plant in an amount that alters the cellulose content in plant. Thus, the invention further provides a genetically altered, e.g., transgenic, plant having an altered cellulose content.

The invention also provides a method to genetically alter plants to increase their disease resistance, e.g., to fungal pathogens. The method comprises introducing an expression cassette comprising a recombinant DNA molecule comprising a nucleotide sequence encoding a 4-coumarate Co-enzyme A ligase operably linked to a promoter functional in a plant cell into cells of a plant. The transformed plant cells are regenerated to provide a genetically altered plant. The recombinant DNA molecule is expressed in the cells of the regenerated, genetically altered plant in an amount effective to render the plant resistant to disease.

Preferably, the recombinant DNA molecule is expressed in amount that decreases the amount of lignin in the plant and/or increases the amount of phenolic compounds which are toxic to fungal pathogens. Hence, the invention also provides a transgenic plant, which is substantially resistant to disease. The plant comprises a native 4-coumarate Co-enzyme A ligase gene, and a recombinant DNA molecule comprising a nucleotide sequence encoding 4-coumarate Co-enzyme A ligase operably linked to a promoter functional in a plant wherein the recombinant DNA molecule is expressed in an amount effective to confer resistance to the transgenic plant.

Other features and advantages of the invention will become apparent to those of ordinary skill in the art upon review of the following drawings, detailed description and claims.

Before one embodiment of the invention is explained in detail, it is to be understood that the invention is not limited in its application to the details set forth in the following description of the preferred embodiment. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

The invention pertains to genetically down regulating a lignin pathway 4-coumarate Co-enzyme A ligase (4CL) in a plant. Plants which have been genetically transformed to down regulate 4CL will hereafter be called transgenic plants. Such down regulation can result in faster growing plants. Such down regulation can also result in a reduction in the lignin content of the plants and/or altered lignin structure. Such down regulation can further result in increased cellulose content. Such down regulation may also result in increased disease resistance. Further, by using a specific 4CL promoter, targeted tissue-specific gene expression can be achieved in either the xylem or the epidermal tissues of the plant.

A. 4CL

Figure 1:
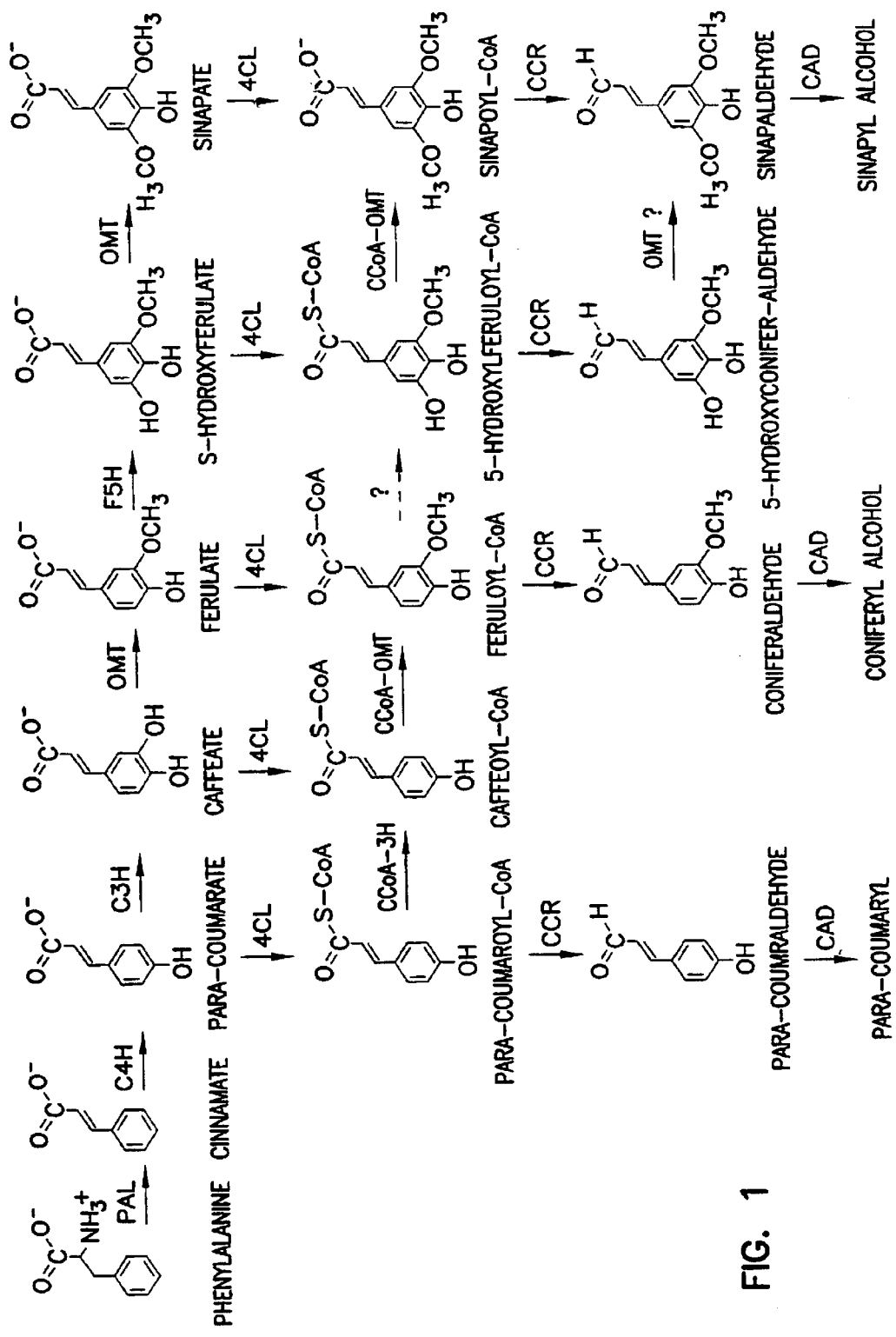
FIG. 1 is a schematic of a phenylpropanoid pathway.

Lignin is synthesized by the oxidative coupling of three monolignols (coumaryl, coniferyl and sinapyl alcohols) formed via the phenylpropanoid pathway as shown in FIG. 1. Reactions in the phenylpropanoid pathway include the deamination of phenylalanine to cinnamic acid followed by hydroxylations, methylations and activation of substituted cinnamic acids to coenzyme A (CoA) esters. The CoA esters are then reduced to form monolignols which are secreted from cells to form lignin.

The products of the phenylpropanoid pathway are not only required for the synthesis of lignin but also required for the synthesis of a wide range of aromatic compounds including flavonoids, phytoalexins, stilbenes and suberin.

In the phenylpropanoid pathway, 4CL activates a number of cinnamic acid derivatives, including 4-coumaric acid, caffeic acid, ferulic acid, 5-hydroxyferulic acid and sinapic acid. The resulting products, CoA esters, serve as substrates for entry into various branch pathways, such as lignin, flavonoids, phytoalexins, stilbenes and suberin. The esterification reactions catalyzed by 4CL require high energy and the reactions are not likely to occur without 4CL. 4CL is important in making a continuous flow of the lignin biosynthesis pathway. 4CL is also important because it is located at the branching points of the phenylpropanoid metabolism. 4CL is suggested to play a pivotal role in regulating carbon flow into specific branch pathways of the phenylpropanoid metabolism in response to stages of development and environmental stress.

The basic properties of 4CL are quite uniform. 4CL depends on ATP as a cosubstrate and requires $Mg^{2+}$ as a cofactor. The optimal pH for 4CL ranges from pH 7.0 to 8.5 and the molecular weight of 4CL isoforms from various plant species ranges from 40 kD to 75 kD. Most 4CLs have high affinity for substituted cinnamic acids. 4CL has the highest activity with 4-coumaric acid.

4CL cDNA sequences have been reported for parsley, potato, soybean, rice, loblolly pine, Arabidopsis, Lithosperum, Vanilla and tobacco. 4CL genes have been isolated and sequenced for parsley, rice, potato and loblolly pine. The analysis of 4CL cDNAs and genes indicates that 4CL is encoded by multiple/divergent genes in rice, soybean, and Lithosperum, very similar genes in parsley, potato, tobacco, and loblolly pine, and a single gene in Arabidopsis.

Two similar 4CL cDNAs in parsley, potato and tobacco have been shown to be expressed at similar level in response to environmental stress and during different developmental stages. Two distinct 4CL cDNAs in soybean and Lithosperum have shown different expression levels when pathogens or chemicals were applied to the cell cultures. It appears that the expression of the 4CL genes is developmentally regulated and inducible by many environmental stresses at the transcription level. 4CL promoters have been isolated and sequenced for parsley, rice and potato.

Alignment of deduced amino acid sequences of cloned plant 4CL sequences reveals two highly conserved regions. The first conserved region (LPYSSGTTGLPK; SEQ ID NO:7), proposed to designate a putative AMP-binding region consists of a serine/theronine/glycine-rich domain followed by a proline/lysine glycine triplet. The second conserved region (GEICIRG; SEQ ID NO:8) contains one common Cys residue. The amino acid sequences of 4CL from plants contain a total of five conserved Cys residues.

The description of the invention hereafter refers to the tree species aspen, and in particular quaking aspen (*Populus tremuloides* Michx), when necessary for the sake of example. However, it should be noted that the invention is not limited to genetic transformation of trees such as aspen. The method of the present invention is capable of being practiced for other plant species, including for example, other angiosperm, and other gymnosperm forest plants species, legumes, gesses, other forage crops and the like.

Preferably, the 4CL down regulation is accomplished through transformation with a homologous 4CL sequence in an antisense orientation. However, it should be noted that a heterologous antisense 4CL sequence could be utilized and incorporated into a plant species to down regulate 4CL if the heterologous 4CL gene sequence has a high nucleotide sequence homology or identity of at least about 70%, more preferably at least about 80%, and more preferably at least about 90%, to the endogenous (native) 4CL gene sequence of that plant species, e.g., a tree species.

In addition, plants transformed with a sense 4CL sequence may also cause a sequence homology-based cosuppression of the expression of the transgene and endogenous 4CL gene, thereby achieving down regulation of 4CL in these plants.

B. Isolation of 4CL cDNAs

The present invention utilizes a homologous 4CL sequence to genetically alter plants. The example described below utilizes a cDNA clone of the quaking aspen 4CL gene to genetically alter quaking aspen.

Two 4CL cDNAs, Pt4CL1 and Pt4CL2, have been isolated from quaking aspen. Pt4CL1 cDNA is lignin pathway-specific and is different from Pt4CL2 cDNA, which is involved in flavonoid synthesis. It should be noted that the methods described below are set forth as an example and should not be considered limiting. The sequences of these 4CL cDNA clones are available from Genbank, Accession Nos. AF041049 and AF041050.

Pt4CL1 and Pt4CL2 genomic clones including their 5'-end regulatory promoter sequences were also isolated. The promotor of Pt4CL 1 (Pt4CL1p) directs xylem tissue-specific gene expression in a plant, whereas the promoter of Pt4CL2 (Pt4CL2p) drives the expression of genes specifically in epidermal tissues of stem and leaf of a plant. These tissue specific promoters will be discussed in more length below.

Young leaves and shoot tips are collected from greenhouse-grown quaking aspen (*Populus tremuloides* Michx). Differentiating xylem is collected from three to four year old quaking aspen. The bark is peeled from the tree exposing the developing secondary xylem on the woody stem. Developing secondary xylem is scraped from the stem and bark with a razor blade and immediately frozen in liquid nitrogen until use.

Total RNA is isolated from the young leaves, shoot tips, and xylem following the method of Bugos et al., Biotechniques 19(5):734–737 (1995). Poly(A)+ RNA is purified from total RNA using Poly(A)+ mRNA Isolation Kit from Tel-test B, Inc. A unidirectional Lambda gt22 expression cDNA library was constructed from the xylem mRNA using Superscript λ System from Life Technologies, Inc. and Gigapack Packaging Extracts from Stratagene. The Pt4CL1 CDNA was obtained by screening the cDNA library with a $^{32}$P-labeled parsley 4CL CDNA probe. The parsley 4CL cDNA (pc4CL2) has Genbank Accession No. X13325.

The Pt4CL2 CDNA was obtained by RT-PCR. The reverse transcription of total RNA isolated form shoot tips was carried out using the Superscript II reverse transcriptase from Life Technologies. Two sense primers (R1S, 5'-TTGGATCCGGIACIACIGGIYTICCIAARGG-3'; SEQ ID NO:9 and H1S, 5'-TTGGATCCGTIGCICARCARGTIGAYGG-3'; SEQ ID NO:10) were designed around the first consensus AMP-binding region of 4CL that was previously discussed. One antisense primer (R2A, 5'-ATGTCGACCICKDATRCADATYTCICC-3'; SEQ ID NO:11) was designed based on the sequence of the putative catalytic motif GEICIRG (SEQ ID NO:12). One fifth of the reverse transcription reaction (4 μl) is used as the template in a 50 μl PCR reaction containing 1× reaction buffer, 200 μM each deoxyribonucleotide triphosphate, 2 μM each R1S and oligo-dT (20 mer) primers, and 2.5 units of Taq DNA polymerase. The PCR reaction mixture was denatured at 94° C. for 5 minutes followed by 30 cycles of 94° C./45 seconds, 50° C./1 minute, 72° C./90 seconds and is ended with a 5 minute extension at 72° C. 2 μl of the PCR amplification products were used for a second run PCR re-amplification using primers H1S and R2A. A 0.6 kb PCR fragment was cloned using the TA Cloning Kit from Invitrogen and used as a probe to screen an aspen genomic library to obtain the Pt4CL2 genomic clone. Two primers (2A, 5'-TCTGTCTAGATGATGTCGTGGCCACGG-3'; SEQ ID NO:13 and 2B, 5'-TTAGATCTCTAGGACATGGTGGTGGC-3'; SEQ ID NO:14) were designed based on the genomic sequence of Pt4CL2 around the deduced transcription start site and the stop codon. These primers were used to clone Pt4CL2 cDNA by RT-PCR, as described above using total RNA isolated from shoot tips.

The DNA sequences of Pt4CL1 and Pt4CL2 cDNA were determined using Δ Taq Cycle Sequencing kit from Amersham.

The Pt4CL1 cDNA has an open reading frame of 1605 bp which encodes a polypeptide of 535 amino acid residues with a predicted molecular weight of 58.498 kd and pI of 5.9. The nucleotide sequence of the aspen 4CL cDNA clone Pt4CL1 is set forth as SEQ ID NO:1. The deduced amino acid sequence for the aspen 4CL1 protein is set forth as SEQ ID NO:2.

The Pt4CL2 cDNA has an open reading frame of 1710 bp which encodes a polypeptide of 570 amino acid residues with a predicted molecular weight of 61.8 kd and pI of 5.1. The nucleotide sequence of the aspen 4CL cDNA clone Pt4CL2 is set forth as SEQ ID NO:3. The deduced amino acid sequence for the aspen 4CL2 protein is set forth as SEQ ID NO:4.

The aspen Pt4CL1 cDNA shares a 55–69% identity at the nucleotide level and 57–76% identity at the amino acid level with previously reported 4CL cDNAs and genes, whereas the Pt4CL2 cDNA shares a 60–71% identity at the nucleotide level and 58–73% at the amino acid level with other 4CL cDNAs and genes as set forth in the following table.

TABLE 1

Comparison of Pt4CL1 and Pt4CL2 nucleotide and predicted amino acid sequences to each other and other full length 4CL sequences.

| Gene | Comparison with Pt4CL1 (%) | | | Comparison with Pt4CL2 (%) | | |
|---|---|---|---|---|---|---|
| | DNA Identity | Protein Identity | Protein Similarity | DNA Identity | Protein Identity | Protein Similarity |
| Pt4CL1 | | | | 61.3 | 63.4 | 72.7 |
| Pt4CL2 | 61.3 | 63.4 | 72.7 | | | |
| Le4CL1 | 64.5 | 70.7 | 78.1 | 61.8 | 64.6 | 73.4 |
| Le4CL2 | 60.1 | 57.3 | 67.7 | 71.1 | 73 | 77.5 |
| Nt4CL1 | 66 | 74.8 | 83.1 | 61.5 | 65.3 | 74.4 |
| Nt4CL2 | 64.1 | 75 | 82.9 | 62.1 | 66.8 | 76 |
| Os4CL1 | 59.2* | 59.8 | 70.2 | 59.6* | 57.7 | 69.5 |
| Os4CL2 | 54.9 | 57.7 | 67.3 | 63.9 | 66.5 | 73.8 |
| Pc4CL1 | 65.1 | 71.2 | 79.6 | 62 | 64.3 | 73.5 |
| Pc4CL2 | 65 | 71.4 | 79.6 | 62.9 | 64.5 | 73.5 |
| Ptd4CL1 | 66.6 | 73.7 | 82.2 | 64.5 | 66.6 | 75.8 |
| Ptd4CL2 | 67 | 74.2 | 81 | 63.4 | 64.7 | 73.3 |
| At4CL | 63.7 | 69.9 | 78.7 | 62.4 | 61.1 | 70.2 |
| Lp4CL | 60.1 | 64 | 73.9 | 62.3 | 67.9 | 77.8 |
| St4CL1 | 69.1* | 74 | 81.4 | 62.2* | 65.3 | 74.5 |
| Vp4CL | 65.2 | 75.5 | 81.6 | 61.5 | 66.5 | 74.1 |

Pt4CL1 and Pt4CLW: aspen 4CL
Le4CL1 and Le4CL2: lithospermum erythrorhizon 4CL
Nt4CL1 and Nt4CL2: tobacco 4CL
OS4CL1 and Os4CL2: rice 4CL (*.DNA sequence compared to Os4CL1 coding region only)
PC4CL1 and Pc4CL2: Parsley 4CL
Ptd4CL1 and Ptd4CL2: hybrid poplar 4CL
At4CL: Arabidopsis 4CL
Lp4CL: lobolly pine 4CL
St4CL: potato 4CL (*.DNA sequence compared to coding region only)
Vp4CL: vanilla 4CL In a study to characterize lignification in aspen stems, it was observed that the lignin composition in the top four internodes (referred to as top internodes hereafter) was different from that in the fifth and subsequent internodes, suggesting the involvement of developmentally regulated differential expression of lignin pathway genes during the transition from primary to secondary growth in aspen stem. To investigate whether this transition regulates differential expression of 4CL gene members, 4CL genes were cloned from top and lower ($6^{th}$–$10^{th}$) internodes and secondary-developing xylem tissue of aspen stems. Nucleotide sequence analysis revealed that clones derived from lower internodes were identical to Pt4CL1, whereas clones isolated from top internodes could be divided into two groups (T1 and T2). Clones in Group T1 were found identical to Pt4CL1. Clones in group T2 shared 60–75% sequence homology with other plant 4CL genes but were distinct from Pt4CL1 cDNA and designated as Pt4CL2-600. These results together with Northern hybridization analysis suggested that Pt4CL2-600 represents a fragment of another aspen 4CL gene expressed in top internodes.

The results of sequence analysis, phylogenetic tree and genomic Southern blot analysis indicate that Pt4CL1 and Pt4CL2 cDNAs encode two distinct 4CLs that belong to two divergent gene families in aspen. The deduced amino acid sequence for the Pt4CL2 protein contains a longer N-terminal sequence than the Pt4CL1 protein but shows profound similarity in the central and C-terminal portions of protein to the Pt4CL1 protein.

Pt4CL1 and Pt4CL2 cDNAs display distinct tissue-specific expression patterns. The Pt4CL1 sequence is expressed highly in the secondary developing xylem and in the 6th to 10th internodes whereas the Pt4CL2 sequence is expressed in the shoot tip and leaves. These tissue-specific expression patterns were further investigated by fusing promoters of Pt4CL1 and Pt4CL2 genes to a GUS reporter gene. The tissue specific promoters for Pt4CL1 and Pt4CL2 are discussed in more length below.

The substrate specificity of Pt4CL1 and Pt4CL2 is also different from each other as determined using recombinant proteins produced in E. coli. Pt4CL1 utilized 4-coumaric acid, caffeic acid, ferulic acid and 5-hydroxyferulic acid as substrates. Pt4CL2 showed activity for 4-coumaric acid, caffeic acid and ferulic acid but not to 5-hydroxyferulic acid.

Specifically, Pt4CL1 and Pt4CL2 were used to construct expression vectors for E. coli expression. The substrate specificity of Pt4CL1 and Pt4CL2 was tested using fusion proteins produced in E. coli. Two plasmids, pQE/4CL1 and pQE/4CL2, were constructed in which the coding regions of Pt4CL1 and Pt4CL2, respectively, were fused to N-terminal His tags in expression plasmids pQE-31 and pQE-32 (QIAGEN, Chatsworth, Calif.). The recombinant proteins of Pt4CL1 and Pt4CL2 produced by E. coli were approximately 60 kD and 63 kD, respectively.

The two recombinant proteins were tested for their activity in utilizing cinnamic acid derivatives. Pt4CL1 recombinant protein showed 100, 51, 72, 19 and 0% relative activity to 4-coumaric acid, caffeic acid, ferulic acid, 5-hydroxyferulic acid and sinapic acid, respectively. Pt4CL2 recombinant protein exhibited 100, 31, 26, 0 and 0% relative activity to 4-coumaric acid, caffeic acid, ferulic acid, 5-hydroxyferulic acid and sinapic acid, respectively. Neither recombinant protein showed detectable activity to sinapic acid.

The results of the tissue-specific expression pattern and substrate specificity suggests that in addition to the general function of 4CL, Pt4CL1apparently is more related to lignin synthesis in the xylem tissue and Pt4CL2 apparently is more likely involved in flavonoid synthesis and UV protection.

It should be noted that the isolation and characterization of the Pt4CL1and Pt4CL2 cDNA clones is described in Kawaoka et al., Proceedings of the 6th International Conference on Biotechnology in the Pulp and Paper Industry, Vienna, Austria (1995); and in Hu, Wen-Jing, Isolation and Characterization of 4-coumarate: Coenzyme A Ligase cDNAs and Genes from Quaking Aspen (*Populus tremuloides* Michx), Ph.D. Dissertation, Michigan Technological University, Houghton, Mich. (1997); and Tsai et al., Plant Physiol., 117, 101 (1998).

C. Transformation and Regeneration

Several methods for gene transformation of plant species with the 4CL sequence are available such as the use of Agrobacterium, electroporation, particle bombardment with a gene gun or microinjection.

Preferably, a 4CL cDNA clone is positioned in a binary expression vector in an antisense orientation under the control of double cauliflower mosaic virus 35S promoter. The vector is then preferably mobilized into a strain of Agrobacterium species such as *tumefaciens* strain C58/pMP90 and is used as the DNA delivery system due to its efficiency and low cost.

Figure 2:
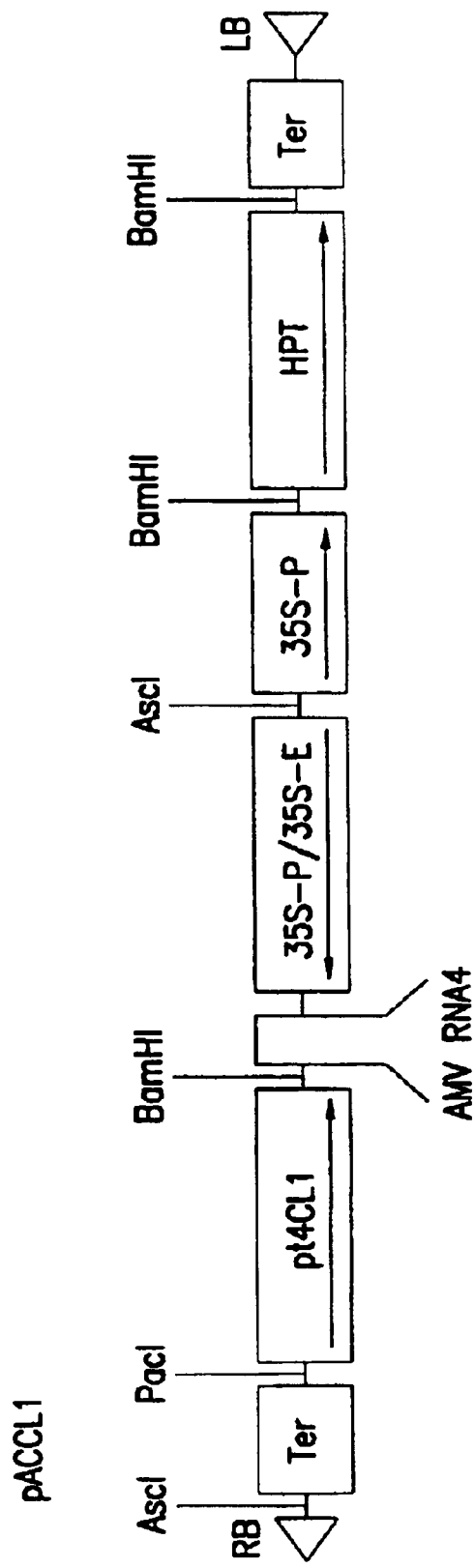
FIG. 2 is a diagram of Agrobacterium T-DNA gene construct pA4CL1.

For example, with reference to FIG. 2, the binary expression pA4CL1 used for plant transformations is shown. Specifically, the Pt4CL1 cDNA is inserted in an antisense orientation into Pac I and BamH I sites between the double CaMV 35S/AMV RNA4 and the 3' terminator sequence of the nopaline synthase gene in a binary cloning vector pA4CL1 (FIG. 2). The binary vector containing hygromycin phosphotransferase (HPT) gene is modified from pBin 19. The gene construct pA4CL1 is available from Michigan Technological University, Institute of Wood Research, Houghton, Mich.

The binary vector construct is mobilized into *Agrobacterium tumefaciens* using the freeze-thaw method of Holsters et al., Mol. Gen. Genet. 163: 181–187 (1978). For the freeze-thaw method, 1.5 ml of overnight cultures *Agrobacterium tumefaciens* strain C58/pMP90 is pelleted at 5000×g for 3 minutes at 4° C. and suspended in 1 ml of ice cold 20 mM $CaCl_2$. To the suspension is added 10 µl binary vector DNA (from an alkaline lysis minipreparation) and mixed by pipetting. The microcentrifuge tube is then frozen in liquid nitrogen for 5 minutes and thawed at 37° C. for 5 minutes. After being cooled on ice, 1 ml of LB is added and the mixture is incubated at 28° C. for 2 hours with gentle shaking. 200 µl of the cells is spread onto LB plates containing gentamycin and kanamycin and incubated at 28° C. for 2 days. Colonies grown on the selection plates are randomly picked or miniprep and restriction enzyme digestion analysis is used to verify the integration.

The resulting binary vector containing Agrobacterium strain is used to transform quaking aspen according to Tsai et al., Plant Cell Rep. 14: 94–97 as set forth below.

Explants of young leaves from cuttings of aspen are obtained by cutting leaf disks of approximately 7 mm square from the young leaves along the midrib of the leaves. The explants are surface sterilized in 20% commercial bleach for 10 minutes followed by rinsing 3 times with sterile distilled, deionized water.

All of the culture media used includes the basal medium of woody plant medium (WPM) as described in Lloyd et al., Proc. Int. Plant Prop. Soc. 30: 421–437 (1980) and supplemented with 2% sucrose. 650 mg/L calcium gluconate and 500 mg/L MES are added as pH buffers as described in Tsai et al., Plant Cell Reports, 1994. All culture media is adjusted to pH 5.5 prior to the addition of 0.75% Difco Bacto Agar and then autoclaved at 121° C. and 15 psi for 20 minutes. Filter sterilized antibiotics are added to all culture media after autoclaving. All culture media are maintained at 23±1° C. in a growth chamber with 16 hour photoperiods (160 $\mu E \times m^{-2} \times S^{-1}$) except for callus induction (as will be described later) which is maintained in the dark.

The sterilized explants are then inoculated with the mobilized vector with an overnight-grown agrobacterial suspension containing 20 µM acetosyringone. After cocultivation for 2 days, the explants are washed in 1 mg/ml claforan and ticarcillin for 2 hours with shaking to kill Agrobacterium. The explants are blotted dry with sterile Whatman No. 1 filter paper and transferred onto callus induction medium containing 50 mg/L kanamycin and 300 mg/L claforan to induce and select transformed callus. The callus induction medium is the basal medium with the addition of 6-benzyladenine (BA) and 2,4-dichlorophenoxyacetic acid (2, 4-D) at concentrations of 0.5 mg/L and 1 mg/L, respectively, to induce callus.

The kanamycin-resistant explants are then subcultured on fresh callus induction media every two weeks. Callus formation occurs after approximately four weeks. Formed calli are separated from the explant and subcultured periodically for further proliferation.

When the callus clumps reach approximately 3 mm in diameter, the callus clumps are transferred to shoot regeneration medium. The shoot regeneration medium is the basal medium containing 50 mg/L kanamycin, 0.5 mg/L thidiazuron (TDZ) as a plant growth regulator and claforan at 300 mg/L to kill Agrobacterium. Shoots were regenerated about 4 weeks after callus is transferred to regeneration medium.

As soon as the shoots are regenerated, they are immediately transferred to hormone-free elongation medium containing 50 mg/L kanamycin and, whenever necessary, claforan (300 mg/L), to promote elongation. Green and healthy shoots elongated to 2–3 cm in length are excised and planted separately in a hormone-free rooting medium containing 50 mg/L kanamycin. The efficient uptake of kanamycin by shoots during their rooting stage provides the most effective selection for positive transformants. Transgenic plants are then transplanted into soil medium of vermiculite:peatmoss:perlite at 1:1:1 and grown in the greenhouse.

The above described transformation and regeneration protocol is readily adaptable to other plant species. Other published transformation and regeneration protocols for plant species include Danekar et al., Bio/Technology 5:587–590 (1987); McGranahan et al., Bio/Technology 6:800–804 (1988); McGranahan et al., Plant Cell Reports 8:512–616 (1990); Chen, Ph.D. Thesis, North Carolina State University, Raleigh, N.C. (1991); Sullivan et al., Plant Cell Reports 12:303–306 (1993); Huang et al., In Vitro Cell Dev. Bio. 4:201–207 (1991); Wilde et al., Plant Physiol. 98:114–120 (1992); Minocha et al., 1986 Proc. TAPPI Research and Development Conference, TAPPI Press, Atlanta, pp. 89–91 (1986); Parsons et al., Bio/Technology 4:533–536 (1986); Fillatti et al., Mol. Gen. Genet 206:192–199 (1987); Pythoud et al., Bio/Technology 5:1323–1327 (1987); De Block, Plant Physiol. 93:1110–1116 (1990); Brasileiro et al., Plant Mol. Bio 17:441–452 (1991); Brasileiro et al., Transgenic Res. 1:133–141 (1992); Howe et al., Woody Plant Biotech., Plenum Press, New York, pp. 283–294 (1991); Klopfenstein et al., Can. J. For. Res. 21:1321–1328 (1991); Leple et al., Plant Cell Reports 11:137–141 (1992); and Nilsson et al., Transgenic Res. 1:209–220 (1992).

D. Phenotype Changes

The results of the transformation can be confirmed with conventional PCR and Southern analysis. Transferring 4CL cDNA in an antisense orientation down regulates 4CL in the plant. Expression of the 4CL has been found to be blocked up to 96 percent of 4CL enzyme activity in some transgenic plants.

In the aspen example, after acclimation, the transgenic aspen displayed an unusual phenotype, including big curly leaves, thick stem diameter, longer internodes, more young leaves in the shoot tip and a red pigmentation in the petioles extending into midvein leaves. Red coloration of the developing secondary xylem tissues is observed after peeling of the bark in the transgenic plants.

E. Accelerated Growth

Down regulation of 4CL altered growth of the transgenic plants. For example, transformation with an antisense 4CL sequence accelerated the growth of the plant. Enhanced growth is markedly noticeable at all ages. In particular the transgenic trees showed enhanced growth in the form of thicker stems and enlarged leaves as compared to control plants. These characteristics are retained in the vegetative propagules of these transgenic trees. Table 2 sets forth exemplary data with respect to several lines of transgenic quaking aspen grown in the greenhouse after eight months. Volume represents the overall quantitative growth of the plant.

TABLE 2

Growth Measurement for Control and Transgenic Plants

| Plant # | Height (cm) | Diameter (cm)* | Volume (cm$^3$)* | Average Length of Internode (cm) |
|---|---|---|---|---|
| Control 1 | 247.7 | 1.08 | 75.6 | 2.6 |
| Control 2 | 250.2 | 1.01 | 66.8 | 2.8 |
| 11-1 | 304.8 | 1.15 | 105.5 | 3.1 |
| 11-2 | 248.9 | 1.01 | 66.4 | 3.4 |
| 11-3 | 241.3 | 0.84 | 44.6 | 3.2 |
| 11-4 | 288.3 | 0.94 | 66.7 | 3.4 |
| 11-5 | 246.4 | 0.92 | 54.6 | 3.3 |
| 11-7 | 226.7 | 1.13 | 75.7 | 3.4 |
| 11-8 | 289.6 | 1.16 | 102.0 | 3.3 |
| 11-9 | 287.0 | 1.76 | 232.6 | 4.3 |
| 11-10 | 252.7 | 0.83 | 45.6 | 3.1 |
| 11-11 | 247.7 | 0.86 | 48.0 | 3.5 |
| 12-1 | 247.7 | 1.1 | 78.4 | 2.7 |
| 12-2 | 199.4 | 0.96 | 48.1 | 2.5 |
| 12-6 | 294.6 | 0.92 | 65.2 | 3.2 |
| 16-1 | 227.3 | 0.95 | 53.7 | 2.8 |
| 16-2 | 278.1 | 0.97 | 68.5 | 3.4 |
| 16-3 | 265.4 | 1.09 | 82.5 | 3.5 |
| 17-2 | 243.8 | 0.89 | 50.5 | 2.6 |

*at 10 cm above ground

The averages for height, diameter, volume and average length between internodes for the control plants are as follows:

| Height (cm) | 248.95 |
|---|---|
| Diameter (cm) | 1.045 |
| Volume (cm$^3$) | 71.2 |
| Ave. Length of Internodes (cm) | 2.7 |

With respect to height alone, for those transgenic plants (11-1, 11-4, 11-8, 11-9, 12-6, 16-2, 16-3) having a statistically larger height than the control plants, the average height was 286.83 cm as compared to the control plant average height of 248.95 cm.

With respect to diameter alone, for those transgenic plants (11-1, 11-7, 11-8, 11-9) having a statistically larger diameter than the control plants, the average diameter was 1.30 cm as compared to the control plant average diameter of 1.045 cm.

With respect to volume alone, for those transgenic plants (11-1, 11-8, 11-9, 12-1, 16-3) having a statistically larger volume than the control plants, the average volume was 120.2 cm$^3$ as compared to the control plant average volume of 71.2 cm$^3$.

With respect to average length of internodes alone, for those transgenic plants (11-1, 11-2, 11-3, 11-4, 11-5, 11-7, 11-8, 11-9, 11-10, 12-6, 16-2, 16-3) having a statistically larger average length of internodes than the control plants, the average length of internodes was 3.39 cm as compared to the control plant average length of internodes of 2.7° cm.

As demonstrated in Table 2, while there are variations in growth among the transgenic plants, the average length of the internodes for the transgenic plants is consistently and significantly higher than that of the control plants. Moreover, there is also faster root initiation, and alterations, e.g., an increase, in root fresh weight and length, i.e., enhanced root growth. Variations in the growth of the transgenic plants is normal and to be expected. Preferably, a transgenic plant with a particular growth rate is selected and this plant is vegetatively propagated to produce an unlimited number of clones that all exhibit the identical growth rate.

F. Lignin

Down regulation of lignin pathway 4CL results in production of plants with reduced lignin content.

The following table shows the reduction of lignin content and 4CL enzyme activity in several transgenic aspen which were transformed with a homologous antisense 4CL sequence.

TABLE 3

Characterization of Transgenic Aspen Plants Harboring Antisense 4CL Sequence

| Transgenic Plant # | Lignin Content % Based on Wood Weight | % Lignin Reduction | % 4CL Enzyme Activity* | % 4CL Enzyme Activity Reduction |
|---|---|---|---|---|
| Control | 21.4 | 0.0 | 868 | 0 |
| 11-1 | 20.5 | 4.2 | 1171 | −25 |
| 11-2 | 19.2 | 10.3 | 515 | 45 |
| 11-3 | 20.9 | 2.3 | 922 | 6 |
| 11-4 | 19.7 | 7.9 | 1032 | −19 |
| 11-5 | 19.7 | 7.9 | 691 | 20 |
| 11-7 | 19.9 | 7.0 | 578 | 38 |
| 11-8 | 20.2 | 5.6 | 694 | 20 |
| 11-9 | 20.4 | 4.7 | 806 | 14 |
| 11-10 | 19.4 | 9.3 | 455 | 51 |
| 11-11 | 20.4 | 4.7 | 726 | 22 |
| 12-1 | 12.8 | 40.2 | 49 | 95 |
| 12-2 | 12.6 | 41.1 | 62 | 93 |
| 12-3 | 11.9 | 44.4 | 61 | 94 |
| 12-6 | 19.8 | 7.5 | 786 | 16 |
| 16-1 | 12.8 | 40.2 | 35 | 96 |
| 16-2 | 20.6 | 3.7 | 780 | 17 |
| 16-3 | 21.0 | 1.9 | 795 | 15 |
| 17-1 | 20.5 | 4.2 | 855 | 9 |
| 17-2 | 21.4 | 0.0 | 925 | 1 |

*activity is expressed as pkat/(mg protein) using 4-coumaric acid as the substrate Lignin content was determined according to Chiang and Funaoka (1990) Holzforschung 44:147–155. 4CL enzyme activity was determined according to Ranjeva et al. (1976), Biochimie 58:1255–1262.

The data in Table 3 demonstrates a correlation between down regulation of 4CL and reduction in lignin content. Transgenic plants with reduced lignin content have an altered phenotype in that the stem is more elastic to the touch or less curly.

It should also be noted that for those transgenic plants (12-1, 12-2, 12-3 and 16-1) with the approximately 40% reduction in lignin content and the corresponding approximately 95% reduction in 4CL enzyme levels, all of those transgenic plants had a consistent deep red coloration in the wood of the plant. Accordingly, the deep red color can be used as an identifier of reduced lignin content.

Down regulation of lignin pathway 4CL can also result in production of plants with an altered lignin structure. Based upon thioacidolysis (Rolando et al. (1992) Thioacidolysis, Methods in Lignin Chemistry, Springer-Verlag, Berlin, pp. 334–349) of plants 12-3 and 16-1, coniferyl alcohol and sinapyl alcohol lignin units are significantly reduced in these two plants as compared to the control tree, as shown in the following table.

TABLE 4

Altered Lignin Structure

| Plant # | Coniferyl Alcohol Units* | Sinapyl Alcohol Units* |
|---|---|---|
| Control | 733 | 1700 |
| 12-3 | 283 | 592 |
| 16-1 | 247 | 445 | micro-mole/g of lignin

The alteration of the frequency of the structural units in lignin of these transgenic plants is evidence that the overall structure of lignin in these plants has been genetically altered.

G. Cellulose Content

Down regulation of lignin pathway 4CL can result in increased cellulose content of the transgenic plants. Analysis of control and transgenic aspen for carbohydrate content demonstrate a higher cellulose content in the transgenic plants than the control plants. Particularly, the transgenic plants that have over 40% lignin reduction have about 10–15% higher cellulose content than the control. Data is set forth in the following tables for trees that were transformed with homologous 4CL in an antisense orientation:

TABLE 5

Analysis of Carbohydrate Components in Transgenic and Control Aspen

| Plant # | Glucan | Arabinan | Galactan | Rhamnan | Xylan | Mannan |
|---|---|---|---|---|---|---|
| Control | 44.23% | 0.47% | 0.79% | 0.37% | 17.19% | 1.91% |
| 11-2 | 49.05% | 0.36% | 1.05% | 0.38% | 15.34% | 2.04% |
| 11-9 | 45.95% | 0.40% | 0.80% | 0.37% | 17.12% | 1.83% |
| 11-10 | 47.49% | 0.43% | 0.99% | 0.40% | 16.24% | 2.35% |
| 12-3 | 50.83% | 0.55% | 1.24% | 0.48% | 17.25% | 1.77% |
| 16-1 | 48.14% | 0.56% | 1.07% | 0.48% | 19.14% | 1.58% |
| 16-2 | 46.55% | 0.34% | 0.82% | 0.37% | 16.75% | 2.31% |

TABLE 6

Comparison of Lignin and Cellulose (glucan) Contents in Transgenic and Control Aspen

| | Lignin | | Cellulose | |
|---|---|---|---|---|
| Plant # | Content % on Wood | % Reduction | Content % on Wood | % Increase |
| Control | 21.4 | 0 | 44.23 | 0 |
| 11-2 | 19.2 | 10.3 | 49.05 | 10.9 |
| 11-9 | 20.4 | 4.7 | 45.95 | 3.9 |
| 11-10 | 19.4 | 9.3 | 47.49 | 7.4 |
| 12-3 | 11.9 | 44.5 | 50.83 | 14.9 |

TABLE 6-continued

Comparison of Lignin and Cellulose (glucan) Contents in Transgenic and Control Aspen

| | Lignin | | Cellulose | |
|---|---|---|---|---|
| Plant # | Content % on Wood | % Reduction | Content % on Wood | % Increase |
| 16-1 | 12.8 | 40.2 | 48.14 | 8.8 |
| 16-2 | 20.6 | 3.7 | 46.55 | 5.2 |
| 11-6 | 18.6 | 13.1 | 45.98 | 3.8 |
| 12-1 | 12.5 | 40.2 | 48.35 | 9.3 |
| 12-2 | 12.6 | 41.1 | 49.74 | 12.5 |
| 12-5 | 14.4 | 32.7 | 45.58 | 3.1 |

The procedure for carbohydrate analysis utilized is as follows. About 100 mg of milled woody tissue powder with sizes that pass a 80-mesh screen was hydrolyzed with 1 mL of 72% (W/W) $H_2SO_4$ for 1 hr at 30° C. Samples were then diluted to 4% (W/W) $H_2SO_4$ with distilled water, fucose was added as an internal standard, and a secondary hydrolysis was performed for 1 hr at 121° C. After secondary hydrolysis, the sugar contents of the hydrolysates are determined by anion exchange high performance liquid chromatography using pulsed amperometric detection. Sugar contents are expressed as % of the weight of the woody tissue used. The above procedures are similar to those in a publication by Pettersen and Schwandt, J. Wood Chem & Technol. 11:495–501 (1991).

H. Increased Disease Resistance

Down regulation of lignin pathway 4CL can result in altered levels of phenylpropanoids or secondary metabolities that display antimicrobial activity. Thus, transgenic plants with down-regulated 4CL can result in enhanced disease resistance, and in particular, with increased fungal pathogen resistance. In particular, greenhouse transgenic aspen plants may show a disease resistance to fungi such as those which induce leaf-blight disease.

I. Promoters

Two distinct genes encoding 4CL and their promoters were cloned. The promoter of Pt4CL1 can drive gene expression specifically in xylem tissue and the promoter for Pt4CL2 confers gene expression exclusively in the epidermal tissues. These promoters can be used to manipulate gene expression to engineer traits of interest in specific tissues of target plants. The significance of the promoters is the application of the xylem-specific promoter to direct the expression of any relevant genes specifically in the xylem for engineering lignin content, lignin structure, enhanced growth, cellulose content, other value-added wood qualities, and the like. The importance of the epidermis-specific promoter is its ability to drive the expression of any relevant genes specifically in epidermal tissues for engineering disease-, UV light-, cold-, heat-, drought-, and other stress resistance traits in plants.

Figure 3:
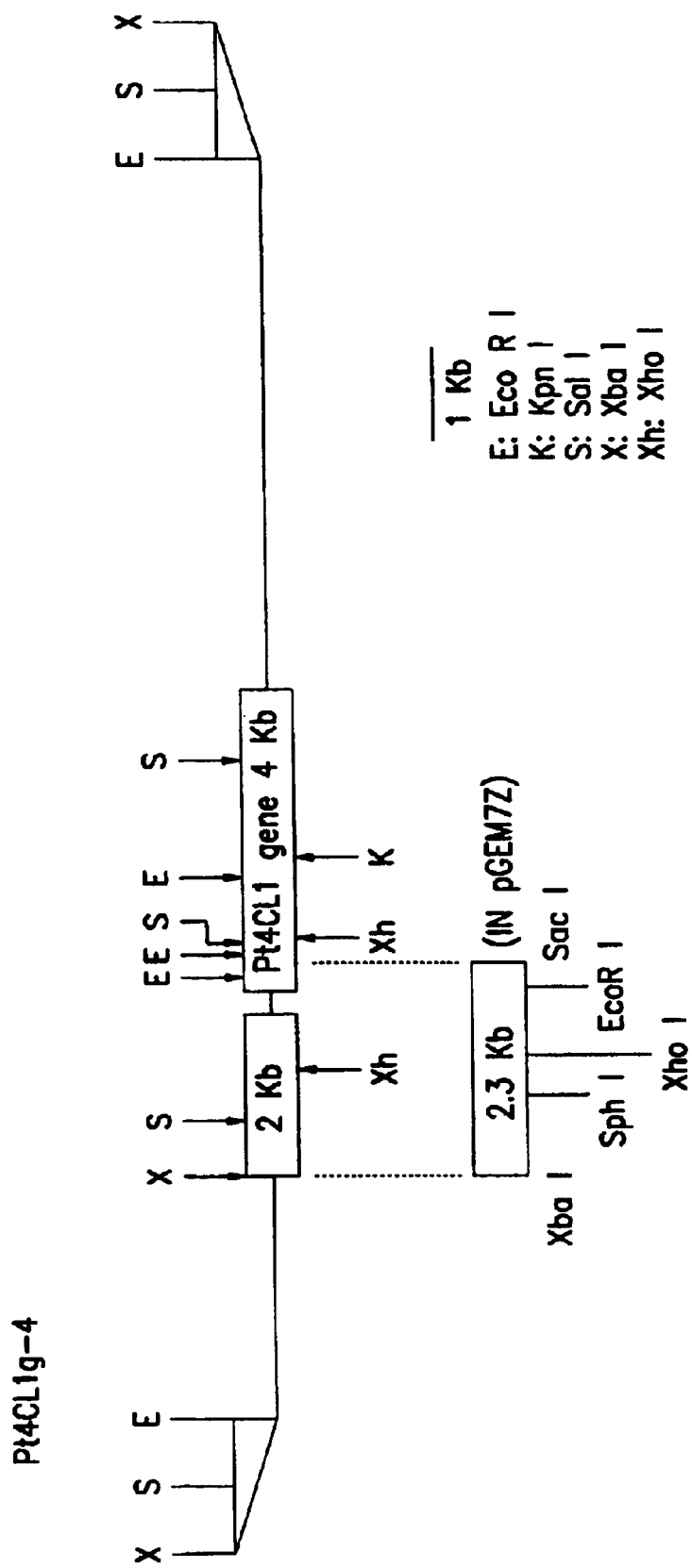
FIG. 3 is a restriction map of genomic clone Pt4CL1g-4.

Specifically, the promoters of the Pt4CL1 and Pt4CL2 were isolated as follows. An aspen genomic library was screened with Pt4CL1 cDNA and Pt4CL2 partial cDNA fragment to isolate genomic clones of Pt4CL1 and Pt4CL2. Eleven and seven positive genomic clones were identified for Pt4CL1 and Pt4CL2 gene, respectively. Among 11 positive clones for Pt4CL1, Pt4CL1g-4 contained a full length coding sequence and at least 2 kb of 5' flanking regions. The restriction map of Pt4CL1g-4 is set forth at FIG. 3.

Figure 4:
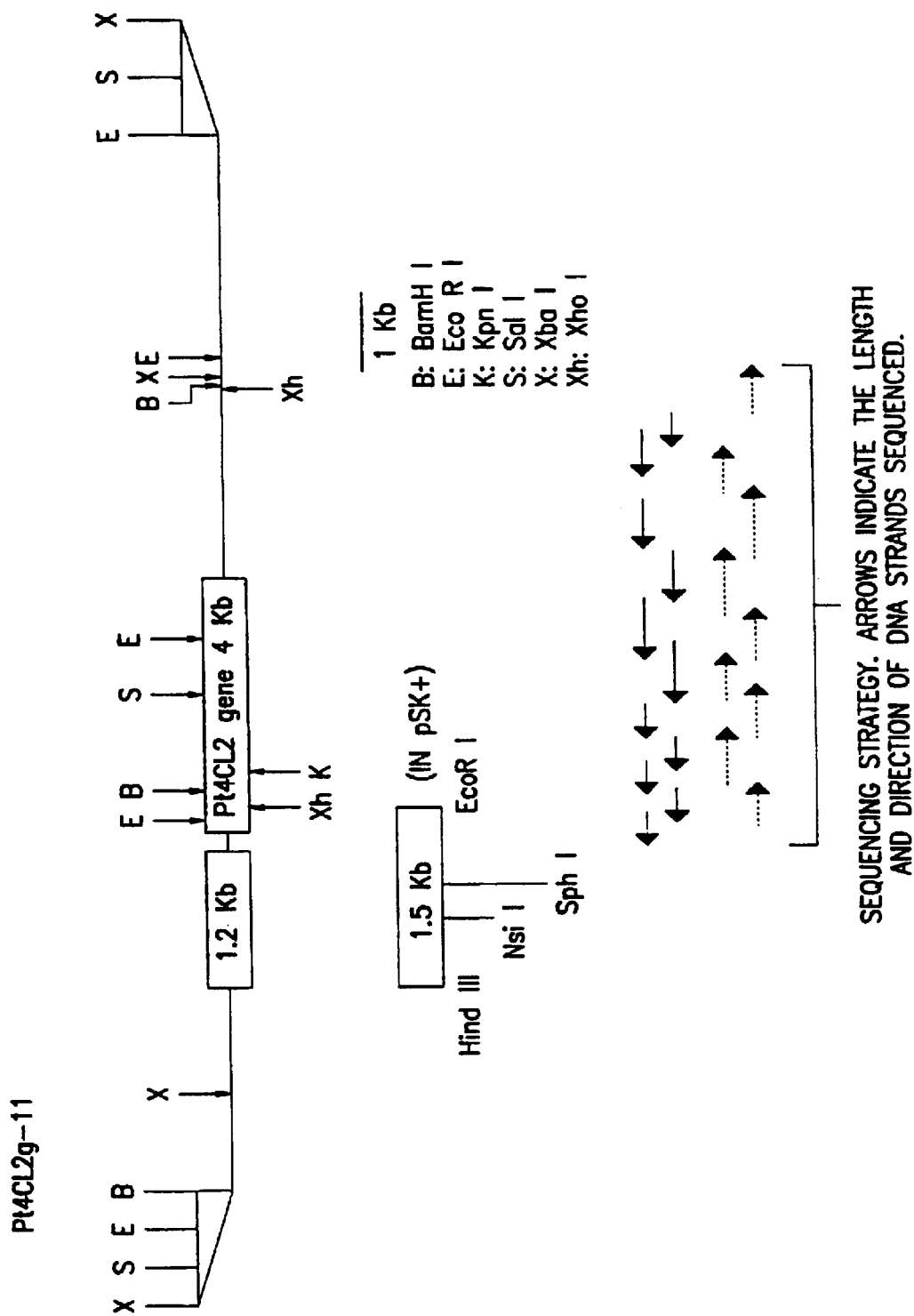
FIG. 4 is a restriction map of genomic clone Pt4CL2g-11.

With respect to Pt4CL2, restriction map analysis was performed on λDNA of positive genomic clone Pt4CL2g-11 which contains a full length coding sequence and about 1.2 kb of 5' flanking region. The restriction map of Pt4CL2g-11 is set forth at FIG. 4.

Figure 5:
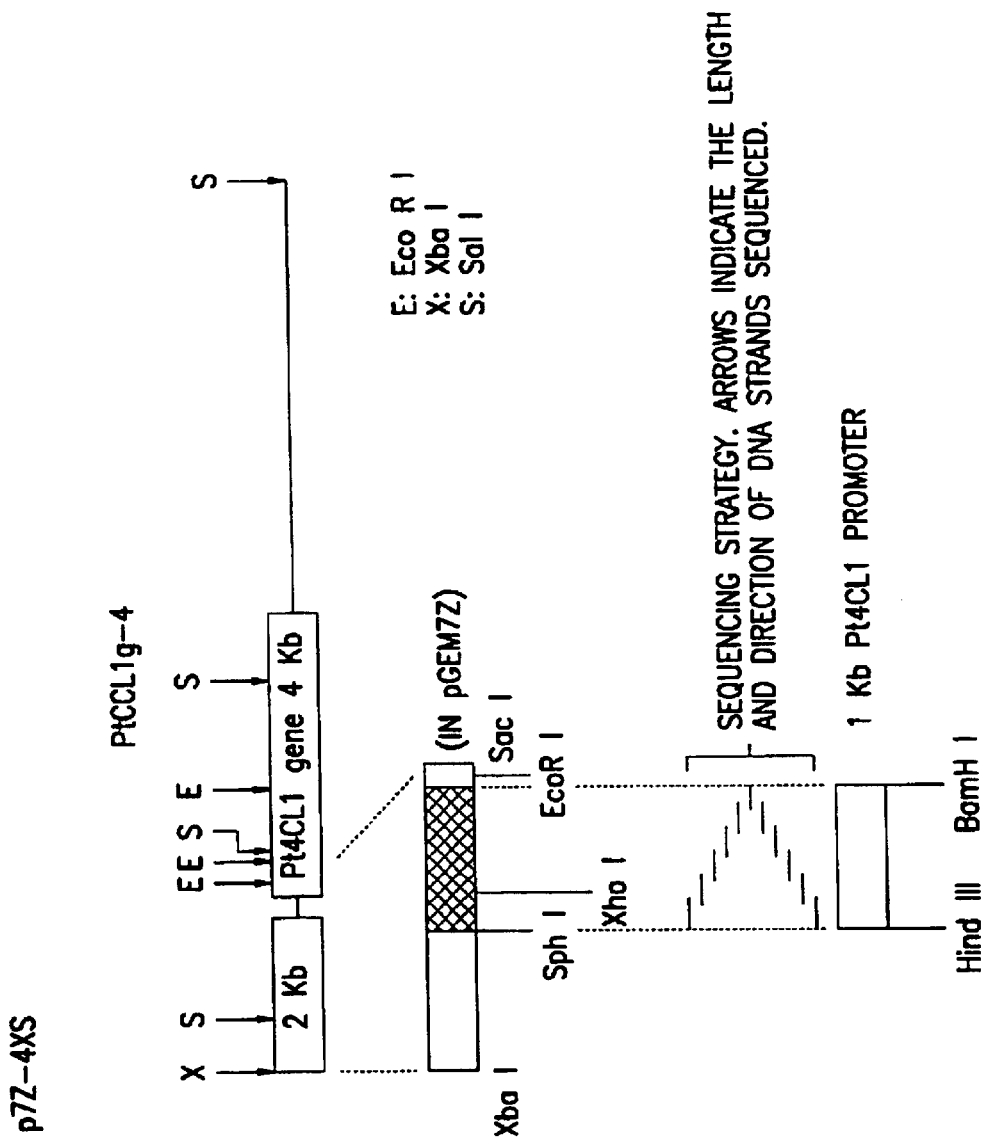
FIG. 5 is a restriction map of subcloned pT4CL1 gene promoter p7Z-4XS.

Approximately a 2.3 kb 5' flanking region of Pt4CL1 was digested from Pt4CL1g-4 using Xba I and Sac I sites and cloned into pGEM7Z Xba I and Sac I sites. The subcloned Pt4CL1 promoter was named p7Z-4XS and the restriction map of P7Z-4XS is set forth at FIG. 5. The 5' unilateral deletion of p7Z-4XS was in generated for DNA sequencing by exonuclease III/S1 nuclease digestion using Erase-a-Base System (Promega, Madison, Wis.). The deletion series was sequenced using a primer on pGEM7Z vector.

Figure 6:
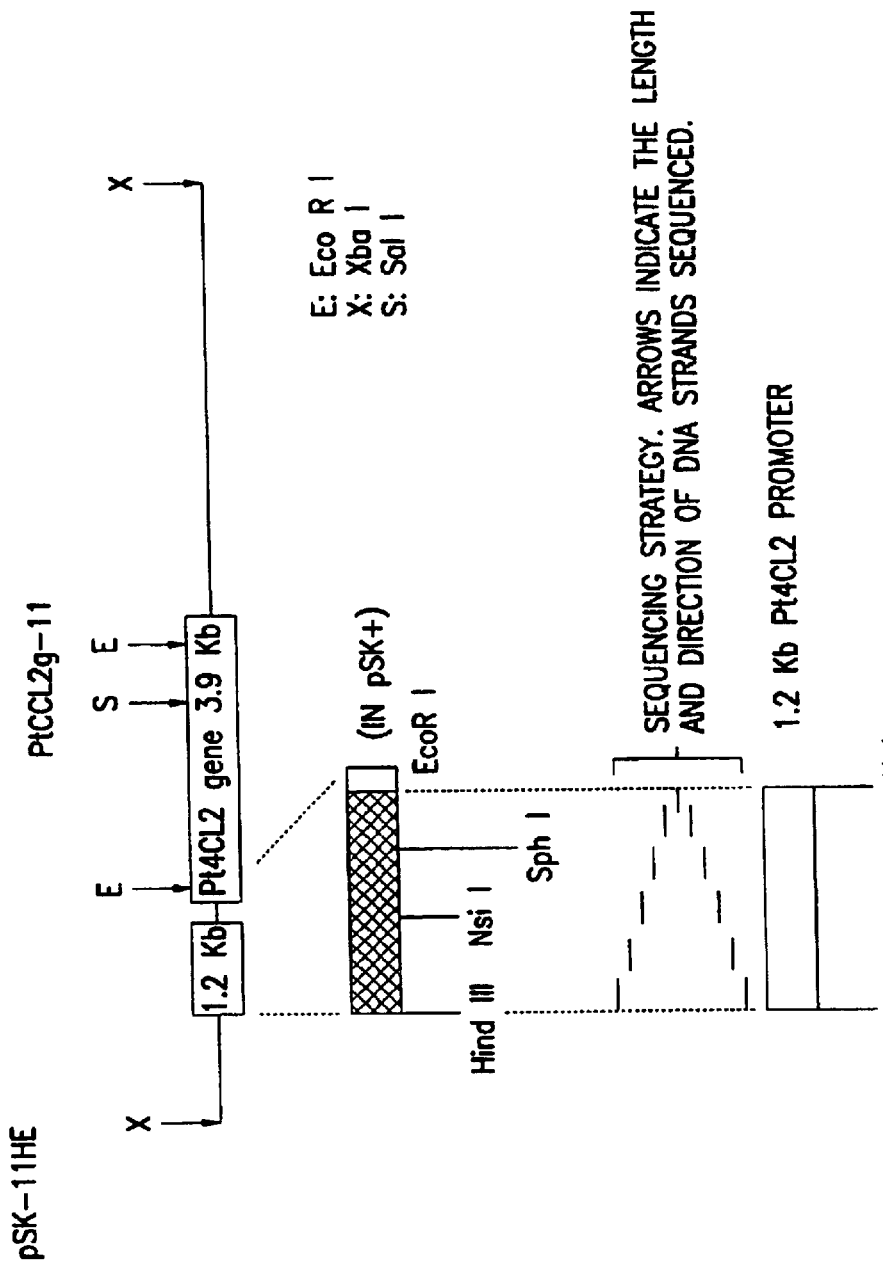
FIG. 6 is a restriction map of subcloned pT4CL2 gene promoter pSK-11HE.

A 1.5 kb Hind III and EcoR I fragment containing a 1.2 kb 5' flanking region of Pt4CL2 and 0.3 kb coding region of Pt4CL2g-11 was subcloned in pBluescript II SK+Hind III and EcoR I sites. The restriction map of the resulting clone, pSK-11HE, was determined by digesting the plasmid with several restriction enzymes, as in set forth at FIG. 6. In order to determine the sequence of the Pt4CL2 promoter, pSK-11HE was further digested into small fragments according to the restriction map and subcloned into vectors with suitable cloning sites. The DNA sequence was determined using M13 universal primer and reverse primer on the vector.

The DNA sequences of the two promoters was determined and analyzed using Δ Taq cycle sequencing Kit (USB, Cleveland, Ohio), and GENETYX-MAC 7.3 sequence analysis software from Software Development Co., Ltd. The nucleotide sequence of promoter region of Pt4CL1 is set forth as SEQ ID NO:5 and the nucleotide sequence of the promoter region of Pt4CL2 is set forth as SEQ ID NO:6. The sequence of the promoter regions of Pt4CL1p and Pt4CL2p is available from Genbank, Accession Nos. AF041051 and AF041052, respectively.

The insignificant sequence similarity between the 5'- and 3'-noncoding regions of these two genes and their distinct exon-intron organizations (four introns in Pt4CL1 and five in Pt4CL2) further substantiate their functional and perhaps evolutionary divergence. Striking differences also were observed in the promoter sequences of these two genes. Three cis-acting elements, box P (CCTTTCACCAACCCCC; SEQ ID NO:15), box A (CCGTTC; SEQ ID NO:16), and box L (TCTCACCAACC; SEQ ID NO:17), previously shown to be consensus in all known plant phenylalanine ammonialyase (PAL) and 4CL gene promoters (Hahlbrook et al., Proc. Natl. Acad. Sci. USA, 92, 4150 (1995); Logemann et al., Proc. Natl. Acad. Sci. USA, 92, 5905 (1995)), were identified within the 1 kb 5' flanking sequence of Pt4CL1 (GenBank Accession No. AF041051). However, none of these boxes could be found within the analyzed 1.2 kb 5' flanking region of Pt4CL2 (GenBank Accession No. AF041052), suggesting that promoter differences between Pt4CL1 and Pt4CL2 genes could be responsible for the strikingly different patterns of tissue-specific expression of these genes, as observed in Northern analysis.

Tissue-specific expression can be achieved by fusing the promoters of Pt4CL1 or Pt4CL2 to a gene, e.g., an open reading frame of interest and transferred to a plant species via Agrobacterium. For the sake of example, the promoters of Pt4CL1 and Pt4CL2 were fused to a GUS reporter gene as detailed below. However, it should be noted that genes other than the GUS reporter gene can be fused to these promoters for tissue specific expression.

In order to construct Pt4CL1 promoter-GUS binary vector, a 1 kb fragment covering 5'-flanking region and 17 bp coding region of Pt4CL1 was subcloned into pGEM7Z Sph I and EcoR I sites for constructing promoter-GUS binary vector. In this 1 kb DNA fragment, it is found that one Xho I site is located at 486 bases upstream to the translation start site and the EcoR I site is located at 17 bases downstream the translation start site. This 0.6 kb fragment was subcloned into pGEM7Z Xho I and EcoR I sites and used as a template in PCR amplification.

In order to construct a promoter-GUS transcriptional fusion, a BamH I site was introduced in front of the translation start site of Pt4CL1 by PCR. PCR amplification was performed using p7Z-4XE as the template, M13 universal primer on pGEM7Z vector as 5' end primer and Pt4CL1p-1 primer containing a BamH I site at the end is complementary to a sequence upstream of the translation start site. The reaction was carried out in 100 µl reaction mix containing 1×pfu reaction buffer, 200 µl each dNTPs, 100 µM each primer and 5 units of pfu. The PCR reaction mixture was denatured at 94° C. for 5 minutes followed by 30 cycles of 94° C. (1 minute), 55° C. (1 minute), 72° C. (1 minute, 30 seconds) and was ended with a 5 minute extension at 72° C.

Figure 7:
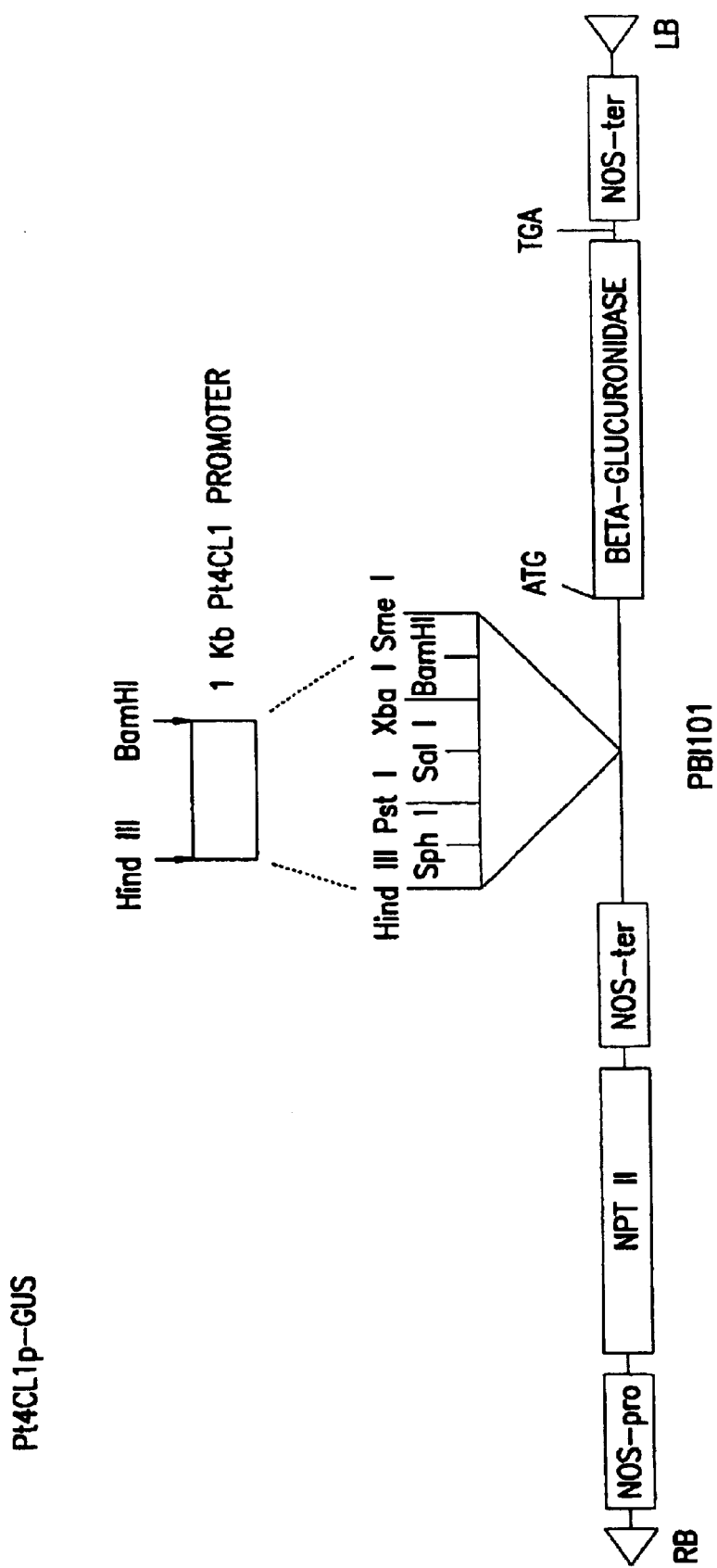
FIG. 7 is an Agrobacterium T-DNA construct of Pt4CL1 promoter and GUS fusion gene Pt4CL1p-GUS.

The amplified 0.6 kb fragment was cloned and sequenced to confirm the sequence. The engineered 0.6 kb fragment was ligated to p7Z-4SE which was digested with Xho I and BamH I. In order to incorporate a Hind III site in the 5' end of Pt4CL1 promoter, the 1 kb Sph I-bamH I PtCCL1 promoter region was the cloned into pNoTA (5 prime-3 prime Inc., Boulder, Colo.) Sph I and BamH I site. The 1 kb Pt4CL1 promoter was then released from pNoTA vector with Hind III and BamH digestion and subsequently transcriptionally fused to pBI101 Hind III and bamH I sites in front of GUS. The resulting binary vector was named Pt4CL1p-GUS and is set forth at FIG. 7.

Figure 8:
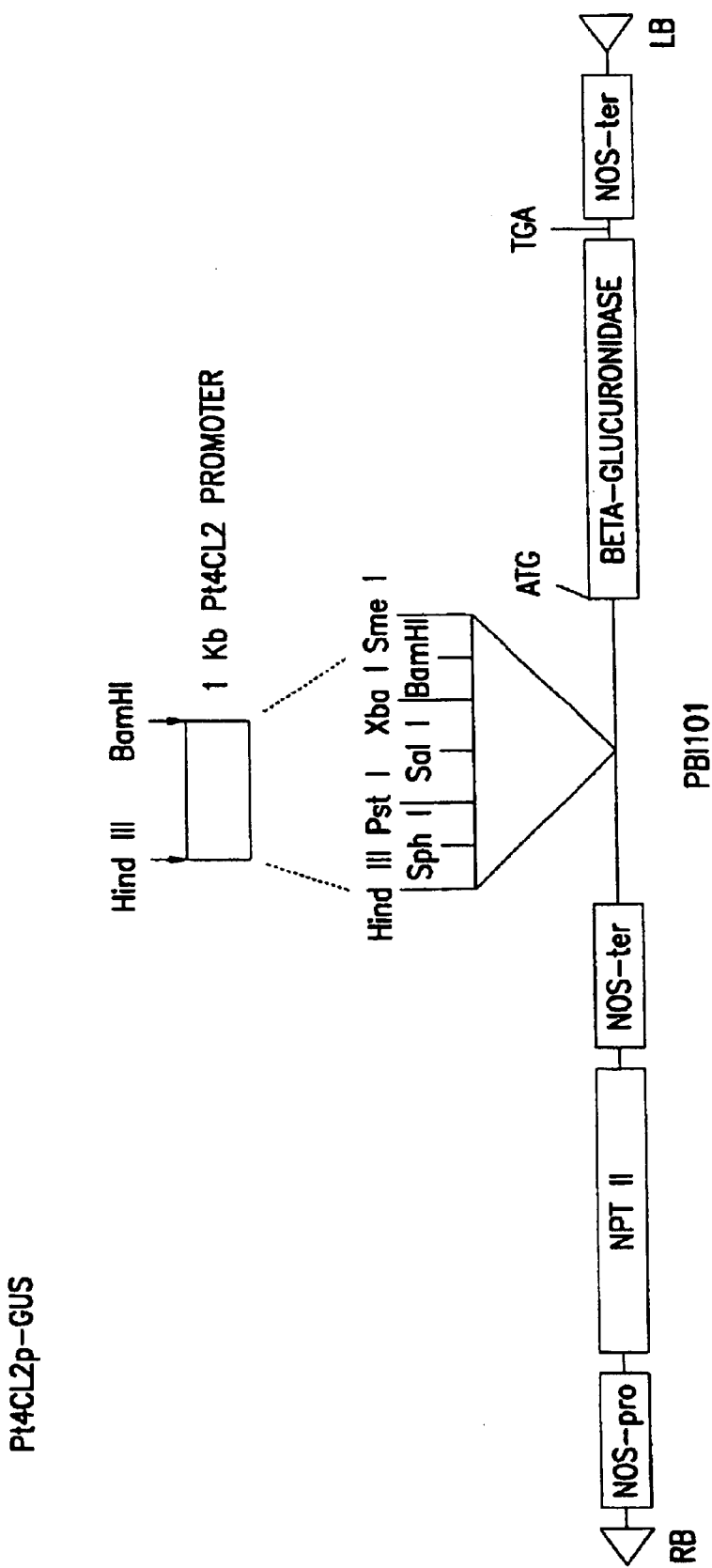
FIG. 8 is an Agrobacterium T-DNA construct of Pt4CL2 promoter and GUS fusion gene, Pt4CL2p-GUS.

In order to construct Pt4CL2 promoter-GUS binary vector, pSK-11HE was digested with Sph I and EcoR I to release 0.2 kb Sph I and EcoR I fragment. The 0.2 kb fragment was cloned into pGEM7Z Sph I and EcoR I sites. A primer, Pt4CL2p-3'(5'-CATCGGATCCTGAGATGGAAGGGAGTTTCT-3'; SEQ ID NO:15) was designed to be complementary to a sequence upstream of the translation start site of Pt4CL2 and to incorporate bamH I site at the end. Amplification was performed using p7Z11SE as a template, M13 universal primer as the 5' end primer and Pt4CL2p3 as the 3' end primer. A PCR reaction was carried out and the amplified PCR product was cloned and sequenced to check the fidelity of the PCR amplification. The 0.2 kb Sph I-bamH I DNA fragment with correct sequence was fused to pSK-11HE linearized with Sph I and BamH I. The resulting plasmid was named pSK-11HB. The promoter of PtCCL2 was then excised from pSK-11HB with Hind III and BamH I and ligated to PBI101 and Hind III and bamH I site to make Pt4CL2p-GUS transcriptional fusion binary vector as shown in FIG. 8.

The Pt4CL1p-GUS and Pt4CL2pGUS constructs were then mobilized into Agrobacterium tumefaciens strain C58/pMP90 by freeze and thaw method as explained previously. Leaf disk transformation of tobacco with these two Agrobacterium constructs is conducted according to the method of Horsch R. B. (1988) Leaf Disk Transformation, Plant Molecular Biology Manual, A5:1–9.

Figure 10A:
FIG. 10. The effects of down-regulation of Pt4CL1 expression on Pt4CL1 activity and lignin accumulation in transgenic aspen. (A) Northern blot analysis of Pt4CL1 transcript levels in control (lane C) and transgenic aspen (3, 4, 5, 6, 8, and 9). Each lane contained 20 $\mu$g of total RNA extracted from developing xylem and the blot was hybridized (Sambrook et al., Molecular Cloning: A Laboratory Manual, Cold Spring Harbor Laboratory Press, NY (1989)) with Pt4CL1 cDNA. (B) Pt4CL1 enzyme activities in developing xylem tissues. Crude protein (40 $\mu$g) extracted from xylem tissue was assayed spectrophotometically for Pt4CL1 activities with various hydroxylated cinnamic acids (Ranjeva et al., 1976). Error bars represent SD values of three replicates. (C) Levels of lignin reduction in woody stem of transgenic lines as compared to the control, based on the lignin contents presented in Table 7. (D and E) Fluorescence microscopy showing transverse sections of the 20$^{th}$ internode from control (D) and transgenic line 6 (E). Lignin autofluorescence was visualized following UV-excitation at 365 nm.
Figure 10B:
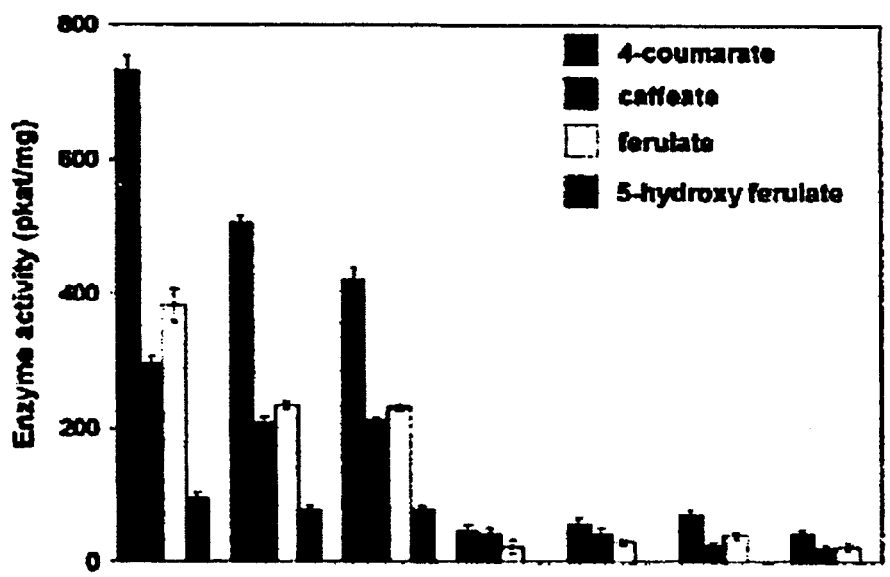
Figure 10C:
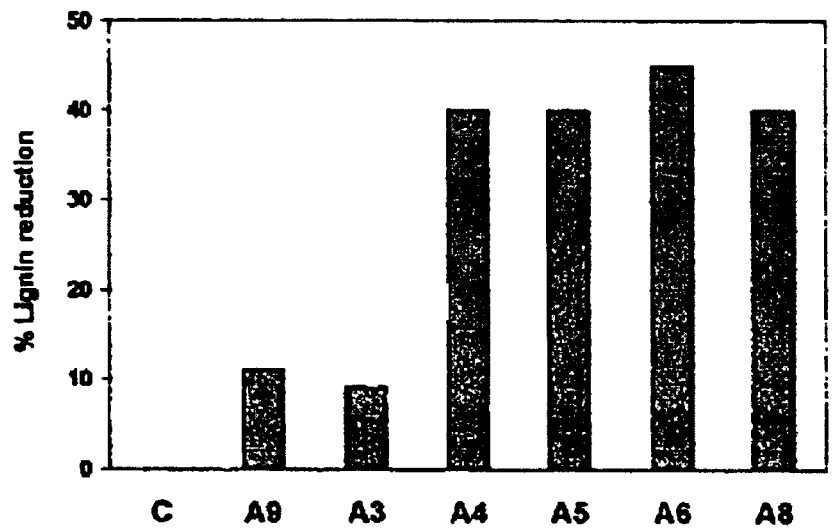
Figure 10D:
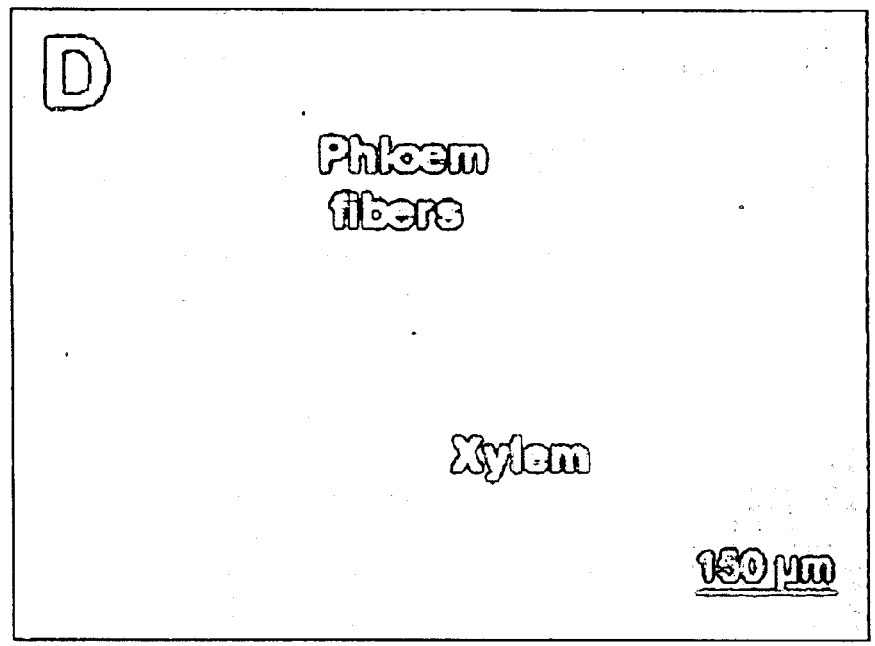
Figure 10E:
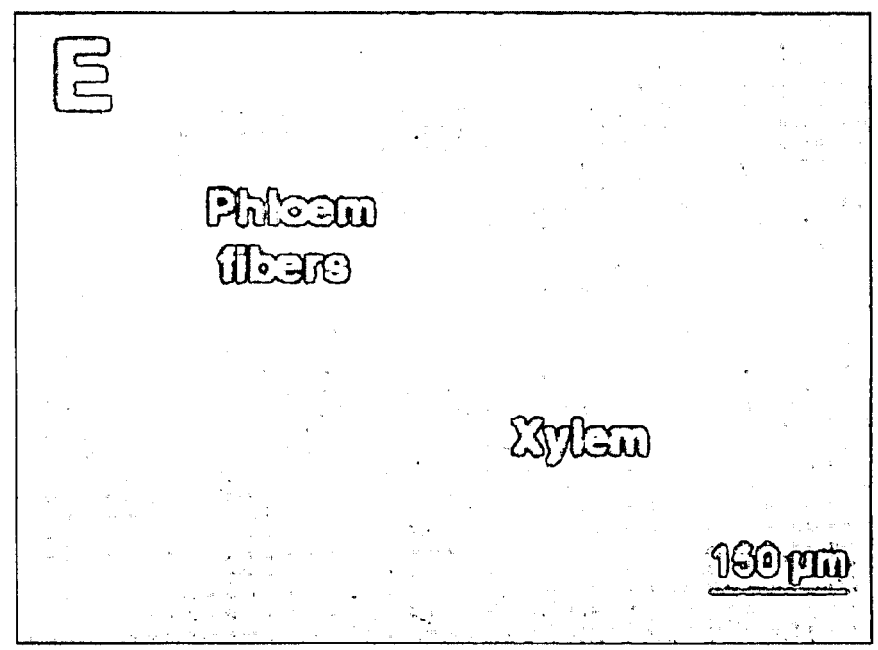

To further investigate the regulation of the tissue-specific expression of Pt4CL1 and Pt4CL2 genes at the cellular level, their promoter activities were analyzed in transgenic tobacco plants by histochemical staining of GUS gene expression driven by a 1 kb Pt4CL1 and 1.2 kb Pt4CL2 promoter sequences, respectively. In Pt4CL1p-GUS transgenic plants, intense GUS staining was detected in lignifying xylem of stem. Strong GUS activity also was found localized to xylem of leaf mid-rib and of root. However, there was no GUS expression in leaf blade, stem epidermis, cortex, phloem and pith, and flower petal. These results are consistent with the evidence that Pt4CL1 gene expression is xylem- or lignifying tissue-specific, and with the observation that Pt4CL1 mRNA level is the highest in aspen secondary developing xylem. In striking contrast to the Pt4CL1 promoter activity, the Pt4CL2 promoter did not direct GUS expression in vascular and xylem tissues in the stem and the leaf of Pt4CL23p-GUS transgenic plants. Instead, it directed GUS expression in lignin-deficient epidermal cells of the stem FIG. 10C) and of the leaf, reflecting the association of Pt4CL2 with nonlignin-related phenylpropanoid biosynthesis in the plant's outer layers. In addition, GUS staining also was detected in Pt4CL2p-GUS transgenic plant's floral organs, such as stigma and petal, suggesting the likely relevance of Pt4CL2 in mediating the formation of flavonoids, which are known to be accumulated in these organs (Higuchi (1997, supra; Caldwell et al., Physiol. Plant, 58, 455 (1983); Shirley, Trends in Plant Sci., 1, 377 (1996)).

The epidermis-specific Pt4CL2 promoter activity indicated that the in vivo Pt4CL2 mRNA message observed in aspen stem internodes could be caused by the signal derived from the epidermis RNA. Thus, the specific expression of Pt4CL2 mRNA in epidermis further supports the biochemical functions of Pt4CL2 protein in the biosynthesis of nonlignin-related phenylpropanoids.

Therefore, the promoter fragments incorporated in Pt4CL1p-GUS and Pt4CL2p-GUS fusion genes must encompass the regulatory sequence elements that are responsible for the contrasting tissue-specific expression between Pt4CL1 and Pt4CL2 genes in aspen. Thus, based on both in vivo gene expression and gene promoter activity analyses, it was concluded that the expression of Pt4CL1 and Pt4CL2 genes in aspen is compartmentalized.

These results demonstrate that in aspen two functionally distinct 4CLs are uniquely compartmentalized by their gene regulatory systems for mediating differentially the biosynthesis of lignin and other phenylpropanoids that serve different physiological functions in aspen. Pt4CL1 is involved in channeling hydroxycinnamic acid derivatives to the synthesis of guaiacyl-syringyl lignin in xylem tissues. Pt4CL2 is associated with the biosynthesis of phenylpropanoids other than lignin in epidermal cells in the stem and the leaf, suggesting its likely participation in disease-resistance or defense-related mechanisms in the plant's outer layers. Therefore, 4CL isoforms may have distinct roles in plant defense systems and in lignification in a tissue-specific manner. From a practical point of view, the tissue-specific Pt4CL1 and Pt4CL2 gene promoters may offer a more defined control of future genetic engineering of traits in trees that must be confined to xylem or epidermal cells.

J. Cellulose Accumulation

Figure 9:
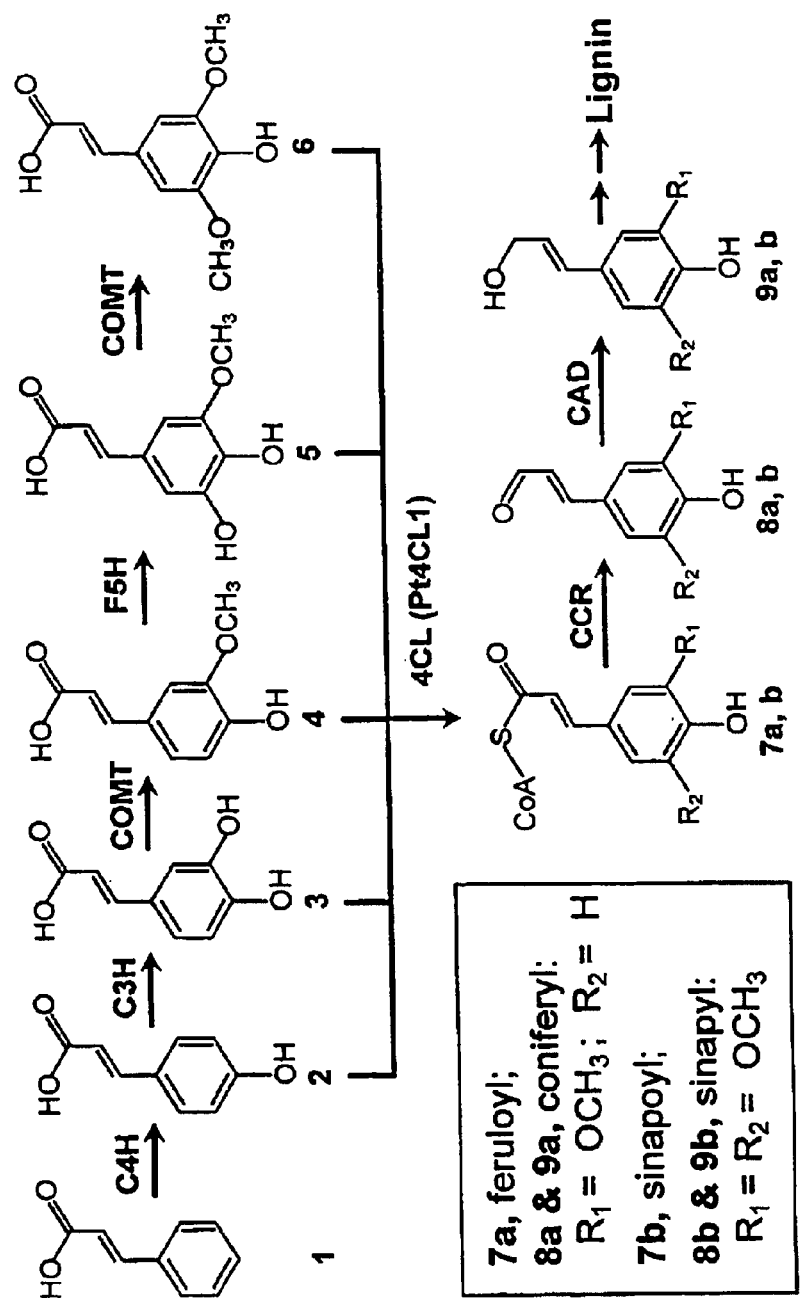
FIG. 9 shows biosynthetic pathways to guaiacyl (coniferyl alcohol 9a) and syringyl (sinapyl alcohol 9b) monolignols for the formation of guaiacyl-syringyl lignin in wood angiosperms. Enzymes are indicated for each reaction step. C4H, cinnamic acid 4-hydroxylase; C3H, 4-coumaric acid 3-hydroxylase; COMT, caffeic acid O-methyltransferase; F5H, ferulic acid 5-hydroxylase; CCR, cinnamoyl-CoA reductase; CAD, cinnamyl alcohol dehydrogenase. Aspen 4CL (Pt4CL1) converts 4-coumaric 2, caffeic 3, ferulic 4, 5-hydroxyferulic 5, and sinapic 6 acids into their corresponding thioesters for the formation of feruloyl-CoA 7a and sinapoyl-CoA 7b, leading to 9a and 9b, respectively.

Twenty-five transgenic aspen lines were generated in which Pt4CL1 expression was down-regulated to various degrees by antisense inhibition, using a Pt4CL1 gene operatively linked to a duplicated enhancer CaMV 35S promoter (Datla et al., Plant Sci., 94, 139 (1993)). The effect of Pt4CL1 deficiency on woody tissue development was investigated in ten-month-old trees. Pt4CL1 messenger RNA was drastically reduced in four lines (FIG. 9A). These lines also exhibited more than a 90% reduction in xylem Pt4CL1 enzyme activity (FIG. 9B), and a 40 to 45% reduction in stem lignin (FIG. 9C). A more modest lignin reduction was found in those lines with less drastic repression of Pt4CL1 activity. The reduction in lignin content was restricted to woody xylem, as shown by attenuated lignin autofluorescence in xylem but not in phloem fibers following UV-irradiation (FIGS. 9D, E). Severe repression of other lignin biosynthetic pathway enzymes, such as COMT or CAD, had no effect on lignin quantity in transgenic aspen, hybrid poplar or a loblolly pine (*Pinus taeda*) mutant (Tsai et al., 1998; VanDoorsselaere et al., Plant J., 8, 855 (1995); Baucher et al., Plant Physiol., 112, 1479 (1996)). Lignin structure, however, was significantly altered in these cases.

To investigate the effect of Pt4CL1 repression on lignin structure, milled wood lignins were isolated from the stem of a transgenic (line 6 with a 45% lignin reduction) and a control (using methods described in Bjorkman, Nature, 174, 1057 (1954); Chiang et al., Holzforschung, 44, 147 (1990); and Ralph et al., JACS, 116, 9448 (1994)) and then were analyzed by nuclear magnetic resonance (NMR) Examination of HSQC (heteronuclear single-quantum coherence) spectra (FIG. 10) and their HSQC-TOCSY (HSQC-total correlation spectroscopy) counterparts and HMQC (heteronuclear multiple-quantum correlation) indicated that these lignins are structurally similar, consistent with their comparable syringyl-to-guaiacyl ratios based on thioacidolysis of intact stem. The ratios for control and transgenic line 6 were 2.3 and 2.1, respectively. Thus, there appeared to be little disruption of the normal lignin structure as a result of reduced Pt4CL1 activity. It is clear from FIG. 10 that $\beta$-aryl ethers ($\beta$-O-4) 10, normally the most abundant (50 to 60%) linkage type in tree lignin (Adler et al., Wood Sci. Technol., 11, 169 (1977)), predominate in both lignin samples. In both lignins, erythro-isomers are more prevalent than their threo- counterparts, typical of angiosperm lignin. Resinol ($\beta$—$\beta$) units (12 FIG. 10), which largely results from coupling of sinapyl alcohol 9b monomers and represent initial intermediates in lignin polymerization reactions in angiosperm trees, are well represented in both lignins. Traces of phenylcoumaran ($\beta$-5) units 11 and $\alpha$-$\beta$-diaryl ethers 14 were detectable in each lignin. Absent from both lignins were condensed biphenyl units such as dibenzodioxocins 13 (Ralph et al., supra). Such units, formed from 5-5-homo-coupling of coniferyl alcohol 9a, normally represent about 4% of the constituents in angiosperm lignin (Adler, supra).

Low levels of 4-coumaric 2 and ferulic 4 acids are sometimes detectable in angiosperm lignins. Therefore, it was determined whether the incorporation of these acids was affected by decreased Pt4CL1 activity. Long-range $^{13}C$-$^{1}H$-correlation (HMQC) NMR experiments revealed that these acids were absent from both lignin samples. However, cell walls of transgenic stem tissue contained alkaline extractable 4-coumaric 2 and ferulic 4 acids at levels 11- and 5-fold higher, respectively, than the control. Alkaline hydrolysis of stem wood meal (pass 80-mesh) was performed at room temperature for 24 hr in 1 N NaOH (Hartley, J. Chromatogr., 54, 335 (1971)). The hydrolysates were neutralized, extracted with ethyl acetate and concentrated. The concentrated products were derivatized with BSTFA and analyzed by GC-MS in SIM (selected ion to monitoring) mode using a DB-5 column. 4-Coumaric acid 2 (TMS-derivative; m/z 308) content of control was 199±13 nmol/g dry wood, and 2145±93 nmol/g dry wood in transgenic line 6. Ferulic acid 4 (CMS-derivative: n/z 338) contents in control and transgenic line 6 were 510±9 and 2431±120 nmol/g dry wood, respectively. No sinapic acid 6 (TMS-derivative: m/z 368) could be detected in control. However, a significant amount of sinapic acid, 2452±119 nmol/g dry wood, was found in transgenic line 6.

Together, the lignin and cell wall analyses support a requirement for activation by Pt4CL1 of these phenolic acids for their incorporation into lignin. The cell wall apparently serves as a sink for accumulating these acids when Pt4CL1 activity is reduced. As a result, lignin content was reduced in the transgenic line but lignin composition and structure were not significantly altered. The conservation of normal lignin composition and structure in the transgenic aspen stands in sharp contrast to the marked changes of lignin composition and structure in other transgenic and mutant plants with altered lignin biosynthesis (Tsai et al., 1998; Van Doorsselaere et al., 1995; Baucher et al., 1996; Elkind et al., Proc. Natl. Acad. Sci. USA, 87, 9057 (1990); Piquemal et al., Plant J., 13, 17 (1998); Sewalt et al., Plant Physiol., 115, 41 (1997); Kajita et al., Plant Physiol., 114, 871 (1997); Lee et al., Plant Cell, 9, 1985 (1997); Dwivedi et al., Plant Mol. Biol., 26, 61 (1994); Ni et al., Transgenic Res., 3, 120 (1994); Atanassova et al., Plant J., 8, 465 (1995); Halpin et al., Plant J., 6, 339 (1994); Hibino et al., Biosci. Biotech. Biochem., 59, 929 (1995)). The results are consistent with the supposition that 4CL modulates lignin accumulation in trees in a regulatory manner that does not result in disruption of lignin structure.

Lignin and polysaccharides are proposed to account for the remarkable mechanical strength of woody tissues (White et al., Nature, 205, 818 (1965); Atalla et al., Science, 227, 636 (1985); Houtman et al., Plant Physiol., 107, 977 (1995); Taylor et al., Plant J., 2, 959 (1992); Turner et al., Plant Cell, 9, 689 (1997)). In consideration of the possible effects of severe lignin reduction on structural polysaceharide components, these components were examined in stem wood tissue. While hemicellulose content remained essentially unchanged, the transgenic lines had a 9 to 15% increase in glucan (Table 7), identified as $\beta$-(1$\rightarrow$4)-glucan, or cellulose, by methylation-based linkage analysis and enzymatic hydrolysis. Lignin content was determined as the sum of Klason and acid-soluble lignins which represent the absolute quantity of lignin (Chiang et al., Holzforschung, 44, 147 (1990)). Cellulose and hemicelluloses contents were determined based on the total sugars after acid hydrolysis of these polysaccharides in stem woody tissue (Chiang et al., Wood Sci. Technol., 17, 217 (1983); Pettersen et al., J. Wood Chem. Technol., 11, 495 (1991)). Wood meal (pass 80-mesh) was vacuum-dried at 45° C. and hydrolyzed with $H_2SO_4$. Sugar contents of the hydrolysates were determined by anion exchange high performance liquid chromatography using pulsed amperometric detection and used for quantifying glucan and other polysaccharides (hemicelluloses) (Davis, J. Wood Chem. Technol., 18, 235 (1998)).

The dried wood meal was also used for methylation analysis of the glucan in wood. Both the Hakomori (J. Biochem. Tokyo, 55, 205 (1964)) and NaOH/$CH_3I$ (Ciucanu et al., Carbohydr. Res., 131, 209 (1984)) methylation procedures were followed. Methylated samples were hydrolyzed in 2M TFA at 121° C. for 2 hr, reduced with sodium borodeuteride, and acetylated using acetic anhydride at 120° C. for 3 hr. The derivatized samples were analyzed by GC-MS using a Sp2330 Supelco column. The methylation revealed that the glucose residues are mainly derived from 1$\rightarrow$4 glucan for both control and transgenic lines. Enzymatic hydrolysis of stem woody tissue further confirmed that the glucans in both control and transgenic lines are $\beta$-(1$\rightarrow$4)-glucan, or cellulose.

Thus, (1$\rightarrow$3)-linked glucan (callose), reportedly deposited in plant cell walls as a result of perturbed secondary metabolism (Schmelzer et al., Plant Cell, 1, 993 (1989)), was not detected in transgenic or control wood. Together, increased cellulose and decreased lignin content resulted in a cellulose-to-lignin ratio of 4 compared with 2 in control aspen (Table 7). The reason for the increased cellulose content is not clear. The absence of change in transcript levels of an aspen homolog of celA encoding a catalytic subunit of cellulose synthase (Arioli et al., Science, 279, 717 (1997)) argues against an increase in the rate of cellulose deposition due to altered transcriptional regulation in transgenic trees with reduced lignin content. The increase in cellulose content suggests that cross talk between lignin and cellulose biosynthetic pathways can nevertheless occur to ensure that cellulose biosynthesis becomes the preferred structural carbon sink when lignin biosynthesis is reduced. Because cellulose and lignin are the two components of wood most responsible for its rigidity, such cross talk could represent an adaptation to sustain mechanical strength in lignin deficient xylem.

Figure 11A:
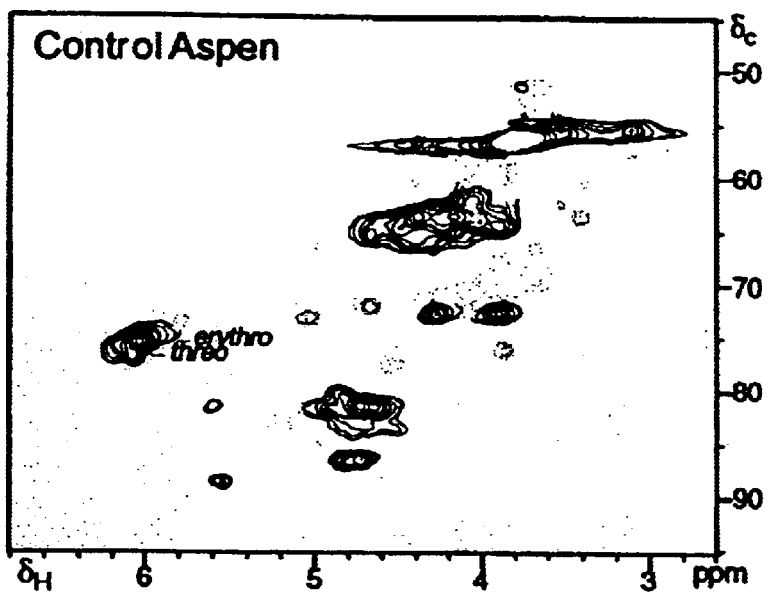
FIG. 11 depicts regions of the HSQC spectra (NMR experiments were performed at 360 MHZ on a Bruker DRX-360 using a narrow bore probe with inverse coil geometry (proton coils closest to the sample) and with gradients. Experiments used were standard Bruker implementations of gradient-selected inverse ($^1$H-detected) HSQC (Palmer et al., J. Magn. Reson. Ser. A, 111, 70 (1991)), HSQC-TOCSY (Braunschweiler et al., J. Magn. Reson., 53, 521 (1983)), and HMQC (Ruiz-Cabello et al., J. Magn. Reson., 100, 282 (1992)) along with the standard 1D $^{13}$C (proton-decoupled) and $^1$H NMR experiments. TOSCY experiments used a 100 ms spin lock period; HMBC used either an 80 or a 100 ms long-range coupling delay.) of isolated milled wood lignins from (A) control and (B) transgenic line 6. Structure assignments (Ralph et al., 1997) reveal the existence of some major structural units in both samples that are common to angiosperm lignin. The erytho- ($\delta_{Ca}/\delta_{Ha}$:75.4/6.05) and threo-($\delta_{Ca}/\delta_{Ha}$:76.6/6.08) isomers of β-aryl ethers 10 are indicated. 5-5-Homo-coupling of coniferyl alcohol 9a involved in dibenzodioxocins 13 ($\delta_{Ca}/\delta_{Ha}$:85.3/4.94) (Ralph et al., 1997) was not detected in either sample. Yellow contours are from intense methoxyl signals and light green contours form xylan residues. Other components (gray contours) in both lignin samples, not relevant or not identified, are commonly seen in many other angiosperm lignin preparations.
Figure 11B:
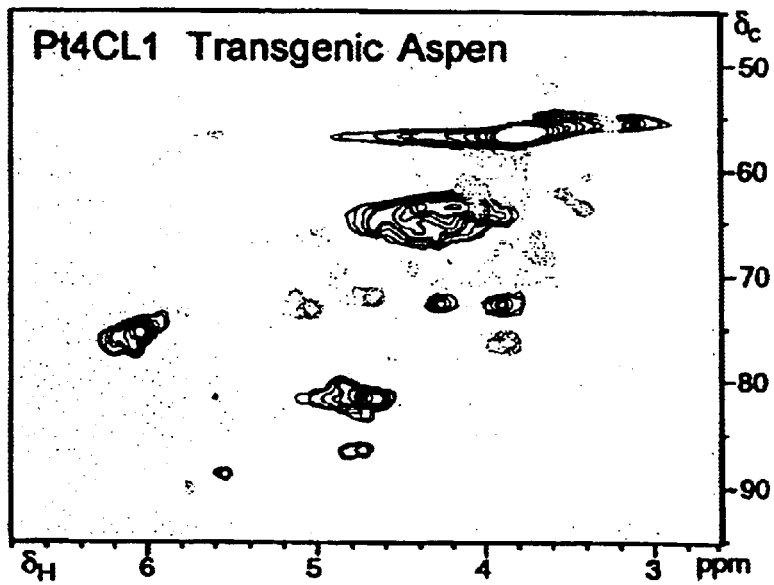
Figure 12A:
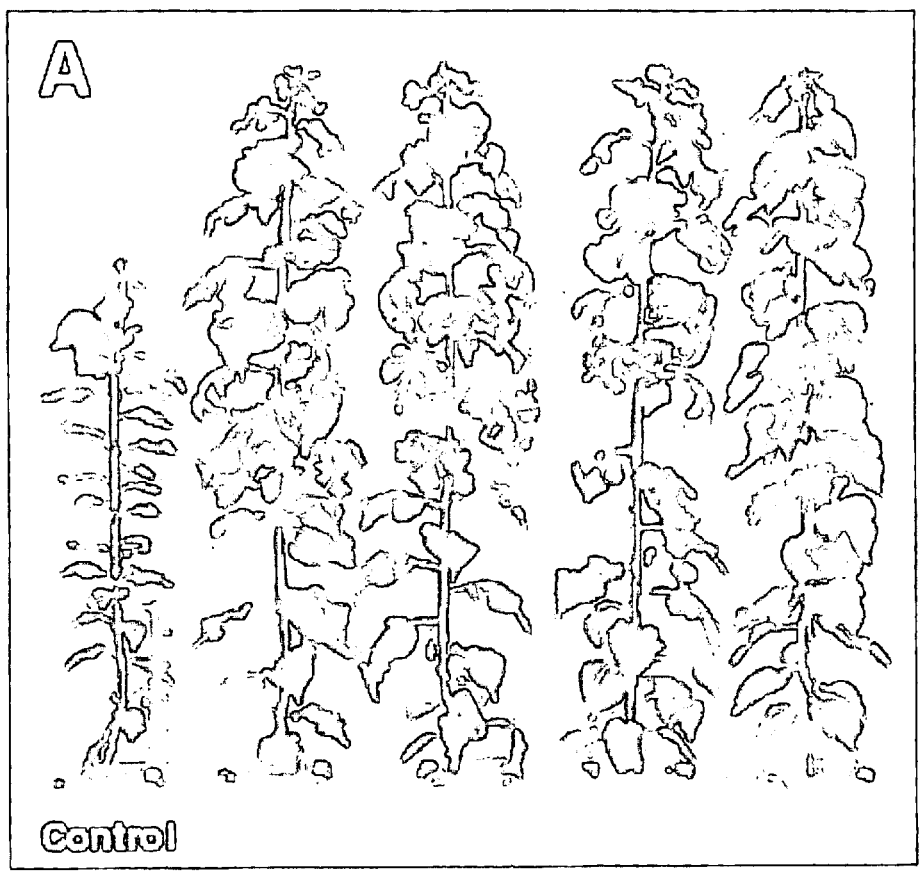
FIG. 12 shows enhanced growth in transgenic aspen. (A) 10-Week-old plants of control and four transgenic aspen grown in a greenhouse (ruler=25 cm). (B) Control and transgenic leaves from the 10$^{th}$ internodes. (C to F) SE images of stem transverse sections of control [C (bar=50 μm) and E (bar=10 μm)] and transgenic line 6 [D (bar=50 μm) and F (bar=10 μm)]. (G) 2-week-old ex vitro rooted stem cuttings from control and transgenic aspen lines 5 and 6. Two cuttings from each line are shown. (H) Leaf upper epidermal cell area. Values represent the mean of at least 100 determinations per leaf. Sample SD was 15 to 20% of the mean for all determinations.
Figure 12B:
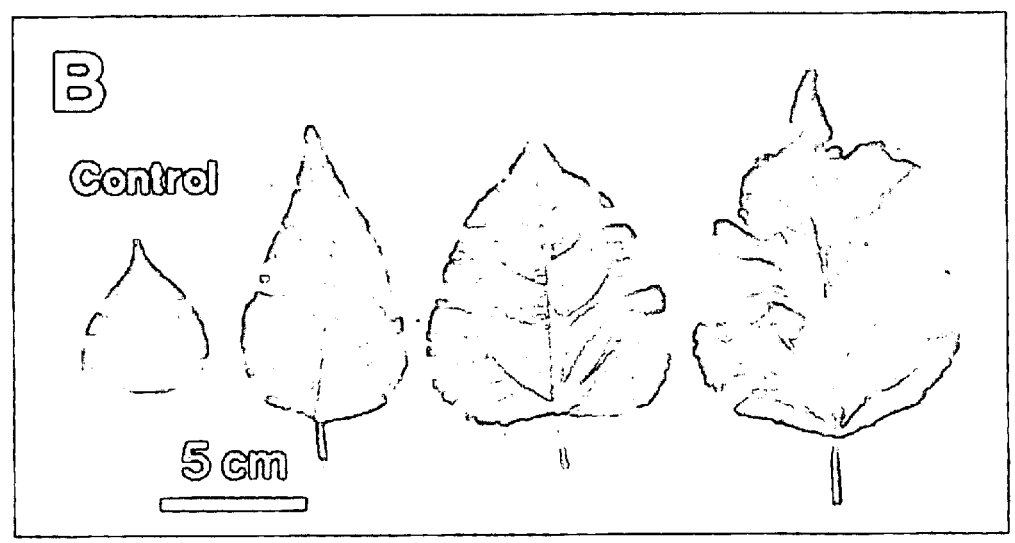
Figure 12C:
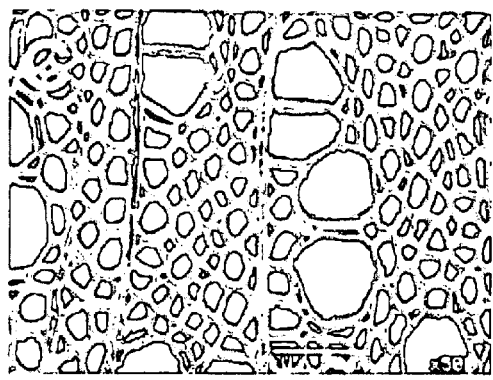
Figure 12D:
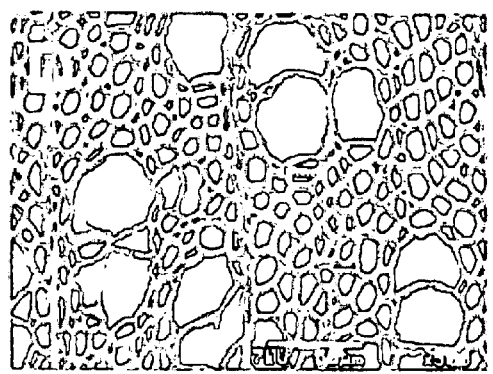
Figure 12E:
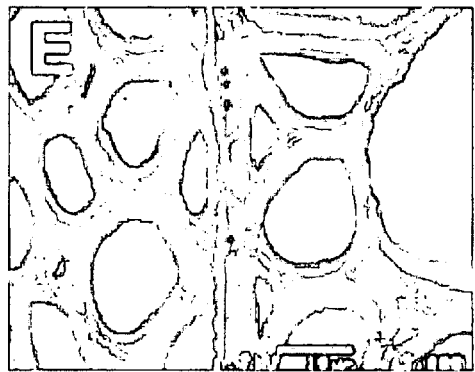
Figure 12F:
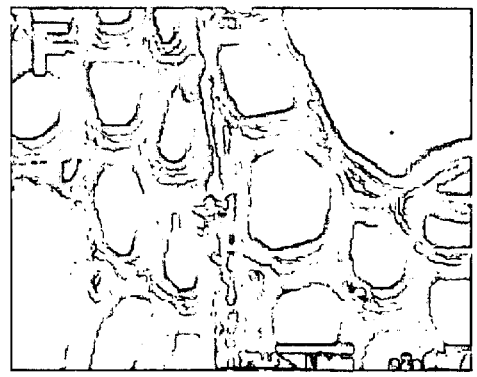
Figure 12G:
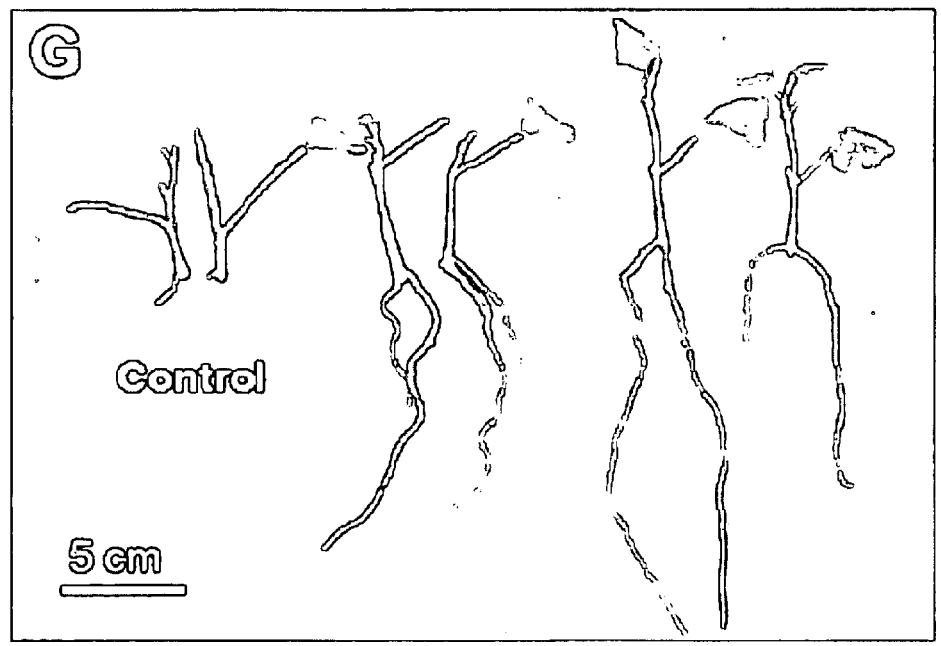
Figure 12H:
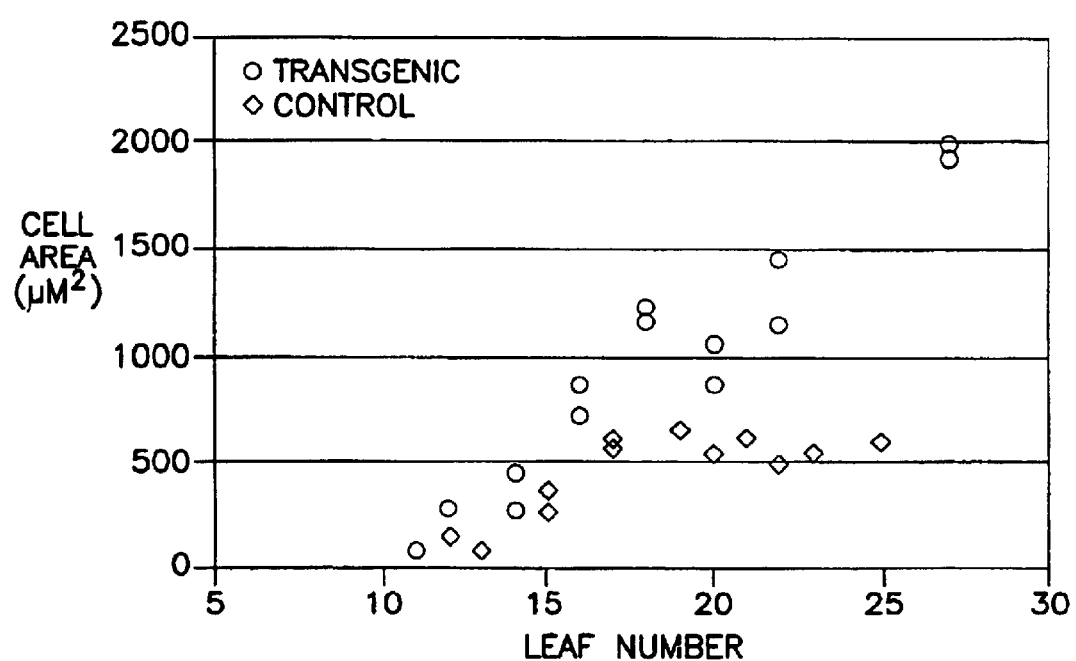

The reduced lignin content in transgenic lines did not adversely affect tree growth and development. In fact, trees with down-regulated Pt4CL1 had thicker stems, longer internodes, and larger (frequently epinastic) leaves than controls (FIGS. 11A and 11B). Scanning electron microscopy (SEM) revealed that the shape and size of sten xylem fiber and vessel cells were similar to those of controls (FIGS. 11C–F). Therefore, the enhanced stem development in these transgenic lines was apparently due to increased proliferative activity during xylem development rather than to increased cell size. Root growth rates also increased in these lines, resulting in greater length (15-fold) and fresh weight gain (20-fold) than in controls over a 14-day period in ex vitro rooting experiments (FIG. 11G). Cell size distribution in the meristematic and elongation zones of root tips was similar in control and transgenic roots. As was the case in stem xylem, increased root growth rate of the transgenic was due to increased cell number. Leaf growth also increased in the transgenic lines resulting in 4- to 5-fold larger leaves than in controls (FIG. 11B). Mature leaf adaxial epidermal cells were measured in two of the transgenic lines and found to be at least twice as large as in control aspen. A more detailed analysis was conducted to determine whether the rate and/or the duration of cell expansion accounted for the increased cell size in mature leaves of transgenic aspen. Epidermal cell expansion stopped at leaf number 15 below the first emerging leaf in control plants, but epidermal cells as well as leaf area continued to expand at leaf number 28 in transgenics (FIG. 11H). Therefore, the prolonged expansion of epidermal cells contributed to increased leaf size in the transgenic aspen lines.

The promotive effects on growth and development in the transgenic trees was a surprising observation. Growth enhancement has not been reported in transgenic tobacco or Arabidopsis with downregulated PAL (phenylalanine ammonia lyase), CCR, C4H, 4CL, COMT, or CAD. In fact, stunted growth and collapsed cell walls occurred in some transgenic tobacco with altered lignin biosynthesis. Whether the growth responses between herbaceous and tree species differed due to altered lignin biosynthesis per se is not clear. In the case of aspen, lignin composition and structure were conserved, eliminating the possibility that altered lignin constituents promoted growth. In aspen trees, reduced expression of Pt4CL1 disrupted lignin biosynthesis downstream of the phenylpropanoid pathway and this increased the concentration of phenylpropanoid intermediates in cell walls. At the same time, enhanced cell division and cell expansion were observed in root tips and leaves. Whether the growth enhancement observed in the transgenic aspen is due to altered carbon distribution between primary/secondary metabolism or specifically due to changes in wall-bound moieties are two possibilities to consider. Histone gene(s) expression has been used as a marker to show that cell division decreases in suspension cells and young leaves of parsley following treatments of that divert carbon flow in to the phenylpropanoid pathway and away from primary metabolic pathways (Logemann et al., Plant J., 8, 865 (1995)). There is also current interest in the organization and composition of cell wall constituents and their effects on cell expansion and plant growth. For these rationale, phenylpropanoid flux as well as cell wall constituents would be of interest for investigating growth effects of lignin manipulation in trees.

The finding that cellulose content increases in transgenic aspen with disrupted lignin biosynthesis is unique; similar observations have not been reported in herbaceous plants (Turner et al., Plant Cell, 9, 689 (1997); Elkind et al., 1990; Piquemal et al., 1998)). Interesting to consider is the idea that in perennial woody plants, lignin and cellulose deposition in cell walls are regulated in a compensatory fashion such that decreased in one are compensated for by increases in the other for maintaining the cellular structural integrity. This compensatory deposition of lignin and cellulose is consistent with the manner of how trees regulate their lignin and cellulose quantities in the course of forming naturally occurring reaction wood for mechanical support. Compensatory regulation such as this would also provide metabolic flexibility during annual growth increments, perhaps key for the long term structural integrity of woody perennials like trees. Further study is required to determine whether such regulation of cellulose accumulation is sensitive to primary/secondary metabolism and to changes in cell wall constituents such as those observed in Pt4CL1 down-regulated aspen.

Overall, lignin limits the utilization of wood for fiber/material-, chemical-, and energy-production. Traditional breeding approaches have not led to trees with more desirable lignin/cellulose composition. However, genetic engineering appears to offer a strategy for manipulating such traits in trees, with the prospect of systemically regulating growth as reported here. The benefit of these engineered traits may also extend to forage crops in which lignin has been identified as the major barrier to their digestibility by ruminants.

TABLE 7

Lignin and cellulose contents in stem woody tissue of control and transgenic aspen. Data are the mean ± SD of three independent experiments. Normalized values relative to control are shown in parentheses.

| Line | Lignin Content (% of dry wood weight) | Cellulose Content (% of dry wood weight) | Cellulose-to-lignin ratio |
|---|---|---|---|
| Control | 21.62 ± 0.30 (100) | 44.23 ± 0.43 (100) | 2.0 |
| 4 | 12.83 ± 0.28 (60) | 48.35 ± 0.60 (109) | 3.8 |
| 5 | 13.02 ± 0.28 (60) | 49.74 ± 0.45 (112) | 3.7 |
| 6 | 11.84 ± 0.08 (55) | 50.83 ± 0.26 (115) | 4.3 |
| 8 | 12.90 ± 0.04 (60) | 48.14 ± 0.29 (109) | 3.8 |

All publications and patents are incorporated by reference herein, as though individually incorporated by reference, as long as they are not inconsistent with the present disclosure. The invention is not limited to the exact details shown and described, for it should be understood that many variations and modifications may be made while remaining within the scope of the invention defined by the claims.

What is claimed is:

1. An isolated and purified DNA molecule comprising SEQ ID NO:5.

2. An expression cassette comprising the promoter sequence set forth in SEQ ID NO:5 operably linked to a coding DNA.

3. The expression cassette as set forth in claim 2, wherein the coding DNA is from a 4-coumarate Co-enzyme A ligase gene.

4. A recombinant polynucleotide comprising a promoter comprising SEQ ID NO:5.

5. A method of expressing a DNA segment in the xylem of a plant, comprising:
   (a) introducing the expression cassette of claim 2 into a plant cell and
   (b) regenerating a transgenic plant from the plant cell wherein the DNA segment is expressed in the xylem of the plant.

6. The method of claim 5, wherein expression of the DNA segment in the xylem of the plant results in agronomically desirable plant traits selected from the group consisting of altered lignin content, increased or decreased coniferyl and sinapyl alcohol units in the lignin structure, altered cellulose content, altered growth or altered cellulose content and combinations thereof.

7. A transgenic plant produced by the method of claim 5.

* * * * *